United States Patent
Li et al.

(10) Patent No.: US 9,987,380 B2
(45) Date of Patent: Jun. 5, 2018

(54) BORON-BASED DUAL IMAGING PROBES, COMPOSITIONS AND METHODS FOR RAPID AQUEOUS F-18 LABELING, AND IMAGING METHODS USING SAME

(75) Inventors: Zibo Li, San Gabriel, CA (US); Francois P. Gabbai, College Station, TX (US); Peter S. Conti, Pasadena, CA (US); Todd W. Hudnall, College Station, TX (US); Tzu-Pin Lin, College Station, TX (US); Shuanglong Liu, Alhambra, CA (US); Chiun-Wei Huang, Alhambra, CA (US)

(73) Assignee: University of Southern California, Los Angeles, CA (US)

( * ) Notice: Subject to any disclaimer, the term of this patent is extended or adjusted under 35 U.S.C. 154(b) by 169 days.

(21) Appl. No.: 13/549,309

(22) Filed: Jul. 13, 2012

(65) Prior Publication Data
US 2013/0189185 A1    Jul. 25, 2013

Related U.S. Application Data

(60) Provisional application No. 61/508,497, filed on Jul. 15, 2011.

(51) Int. Cl.
| | |
|---|---|
| A61K 51/00 | (2006.01) |
| A61M 36/14 | (2006.01) |
| A61K 51/04 | (2006.01) |
| A61K 49/00 | (2006.01) |
| C07F 5/02 | (2006.01) |

(52) U.S. Cl.
CPC ...... *A61K 51/0446* (2013.01); *A61K 49/0002* (2013.01); *A61K 49/0021* (2013.01); *A61K 51/0423* (2013.01); *A61K 51/0455* (2013.01); *C07F 5/022* (2013.01); *A61K 51/00* (2013.01)

(58) Field of Classification Search
USPC ....................................................... 424/1.89
See application file for complete search history.

(56) References Cited

U.S. PATENT DOCUMENTS

2011/0286922 A1    11/2011   Cuthbertson et al.

FOREIGN PATENT DOCUMENTS

| WO | 2010048144 A2 | 4/2010 |
|---|---|---|
| WO | 2010125907 A1 | 11/2010 |
| WO | 2012074840 A2 | 6/2012 |

OTHER PUBLICATIONS

Worsfold et al. (Biosensors Bioelectronics 2004, 19, 1505-1511).*
Murphy et al. (PNAS 2008, 105, 9343-9348).*
Hudnall et al. (J. Fluorine Chem. 2010, 131, 1182-1186).*
Hudnall et al. (Chem. Comm. 2008, 4596-4597).*
Crouzel et al. (J. Labelled Compd. Radiopharm. 1989, XXVII, 1007-1013).*
Kim et al. (J. Chem. Soc. Perkin Trans. 1, 1994, 2357-2358).*
Li et al. (Bioorg. Med. Chem. Lett. 2008, 18, 3112-3116).*
Theoretical Geochemistry: Applications of Quantum Mechanics in the Earth and Mineral Sciences, John A. Tossell, Oxford University Press, USA, Mar 11, 1992 (table 8.6, p400).*
Xie et al., "Synthesis and phamacological characterization of novel fluorescent histamine H2-receptor ligands derived from aminopotentidine" Bioorganic & Medicinal Chemistry Letters, vol. 16, No. 15, pp. 3886-3890, Aug. 1, 2006.
Ono et al., "Development of dual functional SPECT/fluorescent probes for imaging cerebral beta-amyloid plaques" Bioorganic & Medicinal Chemistry Letters, vol. 20, No. 13, pp. 3885-3888, Jul. 1, 2010.
Ting et al., "Fast 18F Labeling of a Near-Infrared Fluorophore Enables Positron Emission Tomography and Optical Imaging of Sentinel Lymph Nodes" Bioconjugate Chem., vol. 21, No. 10, pp. 1811-1819, Oct. 20, 2010.
Hama et al., "Targeted optical imaging of cancer cells using lectin-binding BODIPY conjugated avidin" Biochemical and Biophysical Research Communications vol. 348, No. 3, pp. 807-813, Sep. 29, 2006.

(Continued)

*Primary Examiner* — Michael G Hartley
*Assistant Examiner* — Melissa J Perreira
(74) *Attorney, Agent, or Firm* — DLA Piper LLP (US)

(57) ABSTRACT

A composition useful as a PET and/or fluorescence imaging probe a compound a compound of Formula I, including salts, hydrates and solvates thereof:

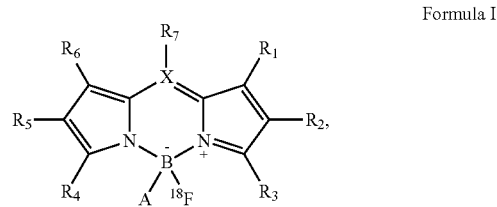

Formula I wherein $R_1$-$R_7$ may be independently selected from hydrogen, halogen, hydroxy, alkoxy, nitro, substituted and unsubstituted amino, cycloalkyl, carboxy, carboxylic acids and esters thereof, cyano, haloalkyl, aryl, X is selected from the group consisting of C and N; and A is selected of hydrogen, halogen, hydroxy, alkoxy, nitro, substituted and unsubstituted amino, alkyl, cycloalkyl, carboxy, carboxylic acids and esters thereof, cyano, haloalkyl, aryl, including phenyl and aminophenyl, and heteroaryl.

10 Claims, 13 Drawing Sheets
(7 of 13 Drawing Sheet(s) Filed in Color)

(56) References Cited

OTHER PUBLICATIONS

Li et al., "Radio aqueous [18F]-labeling of a biodipy dye for positron emission tomography/fluorescence dual modality imaging" Chem. Commun., vol. 47, No. 33, pp. 9324-9326, Sep. 7, 2011.
Hendricks et al., "Synthesis of [18F]BODIPY: Bifunctional Reporter for Hybrid Optical/Positron Emission Tomography Imaging" Angewandte Chemie, vol. 51, No. 19, pp. 4603-4606, May 7, 2012.
International search report and written opinion dated Dec. 7, 2012 issued in corresponding PCT application PCT/US2012/046795 cites the foreign patent documents and non-patent literature listed above.

* cited by examiner

BORON-BASED DUAL IMAGING PROBES, COMPOSITIONS AND METHODS FOR RAPID AQUEOUS F-18 LABELING, AND IMAGING METHODS USING SAME

STATEMENT REGARDING FEDERALLY SPONSORED RESEARCH OR DEVELOPMENT

This invention was made with government support under Contract No. DE-SC0002353 awarded by the Department of Energy, Contract No. P30CA014089 awarded by the National Cancer Institute, and contract No. CHE-0952912 awarded by the National Science Foundation. The government has certain rights in the invention.

BACKGROUND OF THE INVENTION

[$^{18}$F]-Positron emission tomography (PET) is a powerful imaging technique[1] which provides in viva information on the distribution of radiolabeled biomolecules. Despite numerous advantages, this technique remains affected by two major limitations. First, the short-lived $^{18}$F-radionuclide needs to be incorporated into molecules as expediently as possible. However, $^{18}$F is typically prepared by proton bombardment of [$^{18}$O]-water and is thus obtained as the anion in an aqueous/non-nucleophilic form.[2] Second, the PET imaging technique is characterized by relatively low spatial resolution (1-2 mm).[2]

To address the first challenge, a great deal of effort has been devoted to the development of aqueous fluorination protocols based on fluorophilic elements such as silicon and aluminum. The second challenge can be addressed by combining PET imaging with a second imaging technique such as fluorescence which offers much higher spatial and temporal resolution.[4]

However, there remains a need for the fast and efficient radiolabeling. There also remains a need for combination imaging probes that combine PET with fluorescence imaging capabilities.

SUMMARY OF THE INVENTION

One object of the present invention is directed to PET/fluorescence dual modality agents having both a fluorophore and a functional group capable of being rapidly and efficiently radiolabeled.

A composition for use as an imaging probe comprising at least one compound selected from the group consisting of compounds of Formula I, including salts, hydrates and solvates thereof:

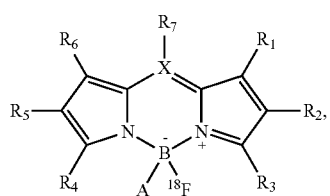

Formula I the compounds of Formula X, including salts, hydrates and solvates thereof

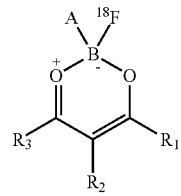

Formula X the compounds of Formula XII, including salts, hydrates and solvates thereof.

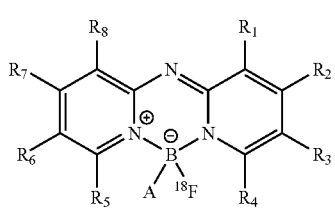

Formula XII wherein $R_1$, $R_2$, $R_3$, $R_4$, $R_5$, $R_6$, and $R_7$ may be independently selected from the group consisting of hydrogen, halogen, hydroxy, alkoxy, nitro, substituted and unsubstituted amino, cycloalkyl, carboxy, carboxylic acids and esters thereof, cyano, haloalkyl, aryl, including phenyl and aminophenyl, azide, alkyne and heteroaryl;

X is selected from the group consisting of C and N;

A is selected from the group consisting of hydrogen, halogen, hydroxy, alkoxy, nitro, substituted and unsubstituted amino, alkyl, cycloalkyl, carboxy, carboxylic acids and esters thereof, cyano, haloalkyl, aryl, including phenyl and aminophenyl, and heteroaryl.

Another embodiment of the present invention is directed to a pharmaceutical composition for use in PET and/or fluorescence imaging comprising a radiolabelled composition according to the present and a pharmaceutically acceptable carrier. Preferably, the composition is dispersed or dissolved in a liquid medium suitable for injection.

Another embodiment of the present invention is a method of PET and/or fluorescence imaging comprising administering to a patient in need thereof an effective amount of the radiolabelled compositions according to the present invention, and scanning the subject with at PET and/or fluorescence imaging device, wherein the detection of a PET or fluorescence signal corresponds to an image of a tissue of the subject.

Another embodiment of the present invention is a method for studying the localization of PET probes within a tissue of a subject comprising: administering to the subject an effective amount of the composition according to claim 1, the composition being a dual PET/fluorescence imaging agent, subjecting a tissue of the subject to irradiation of an electromagnetic radiation, wherein the electromagnetic radiation is absorbed by the composition, detecting fluorescence of the composition of claim 1 within the tissue, wherein the fluorescence of the composition within the tissue is indicative of the presence of a PET probe within the tissue.

Another embodiment of the present invention is directed to a composition useful for PET and/or fluorescence imaging comprising a radiolabelled compound according to the present inventionconjugated to a targeting moiety. In a preferred embodiment, the targeting moiety is a peptide, preferably an RGD peptide. The RGD peptide may be a cyclic RGD peptide.

Another embodiment of the present invention is directed to a fast and efficient method for labeling a compound with [$^{18}$F] or [$^{19}$F}. The method comprises combining a compound comprising at least one boron-fluorine bond with a [$^{18}$F]/[$^{19}$F} source reagent in the presence of one or more Lewis Acids in a solvent. The method according to claim 15, wherein the compound, the source reagent and the one or more Lewis acids are dissolved or dispersed in a solvent, preferably a nonaqueous solvent. The Lewis Acid is one or more compounds selected from the group consisting of Suitable Lewis Acids include SnCl4, $ZnCl_2$, $GaCl_3$, $FeCl_3$, $TiCl_4$, $AlCl_3$, $AlF_3$, $InCl_3$, $SnCl_2$, $ScCl_3$, $ZrCl_4$, $CrCl_3$, $CoCl_3$, FeCl, $CoCl_2$, $NiCl_2$, $CuCl_2$, $CH_3CO^+$, $Cu^+$, $Au^+$, $Hg^{2+}$, $Pb^{2+}$, $ZnBr_2$, $ZnF_2$, $ZnI_2$, $ZnMe_2$, $ZnEt_2$, $ZnPh_2$. The at least one Lewis Acid preferably comprises $SnCl_4$.

Another embodiment of the present invention is directed to precursor compounds that comprise a leaving L that can be substituted for either a [$^{18}$F] or [$^{19}$F] according to the methods of the present invention. A composition comprising: comprises at least one compound selected from the group Formula II, including salts, hydrates and solvates thereof:

DESCRIPTION OF THE FIGURES

"The file of this patent contains at least one drawing executed in color. Copies of this patent with color drawings will be provided by the Office upon request and payment of the necessary fee".

DETAILED DESCRIPTION OF THE INVENTION

Definitions

Figure 1:
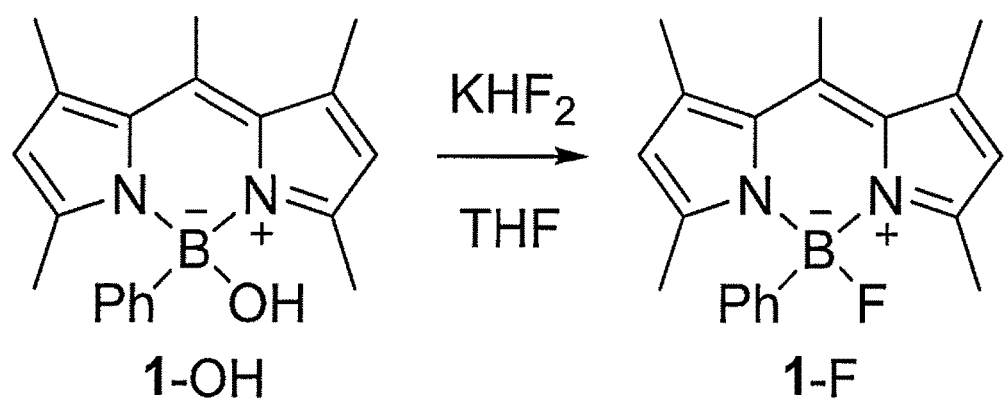
FIG. 1 shows the conversion of compound 1-OH to 1-F by simple reaction with $KHF_2$.

The term "alkyl" herein used means $C_1$-$C_{10}$ straight or branched chain alkyl, for example, methyl, ethyl, n-propyl, i-propyl, n-butyl, i-butyl, sec-butyl, tert-butyl, n-pentyl, i-pentyl, neo-pentyl, tert-pentyl, and the like.

The term "alkoxy", alone or in combination, signifies a group of the formula alkyl-O— in which the term "alkyl" is as defined above, such as methoxy, ethoxy, n-propoxy, isopropoxy, n-butoxy, isobutoxy, sec. butoxy and tert.butoxy, preferably methoxy and ethoxy and most preferred methoxy.

The term "halo" or "halogen" as used herein refers to F, Cl, Br, and I (e.g., fluoro, chloro, bromo, and iodo.).

The term "haloalkyl" signifies a an "alkyl" substituted with one or more halo groups.

The term "aryl" herein used means monocyclic or condensed ring aromatic hydrocarbons. Examples of the aryl are phenyl, naphthyl, and the like.

The term "amino", alone or in combination, signifies a primary, secondary or tertiary amino group bonded via the nitrogen atom.

The term "heteroaryl" herein used means a 5 to 6 membered aromatic heterocyclic group which contains one or more hetero atoms selected from the group consisting of nitrogen, oxygen and sulfur atoms in the ring and may be fused with a carbocyclic ring or other heterocyclic ring at any possible position.

The term "carboxylic acid" means an organic chemical compound comprising at least one carboxylic acid functional group (i.e. —C(O)OH)

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

Dual Modality Imaging Probes and Precursors Thereof

One aspect of the present invention is directed novel [$^{18}$F]-PET/fluorescence dual modality agents, including precursors of the dual modality imaging agents and the synthesis thereof, said agents comprising a compound having both a fluorophore and a radioemitting functional group. In a preferred embodiment, such as those of Formula I, the fluorophore may itself comprise the radioemitting functional group.

According to one embodiment of the present invention, the dual modality imaging agents according to the present invention are analogs of a class of organoboran compounds known as BODIPY dyes. BODIPY, short for boron-dipyrromethene, is a class of fluorescent dyes. It is composed of dipyrromethene complexed with a disubstituted boron atom, typically a $BF_2$ unit. The IUPAC name for the BODIPY core is 4,4-difluoro-4-bora-3a,4a-diaza-s-indacene. Bodipy dyes are generally stable, have high quantum yields and their emission can be tuned into the NIR (near Infrared) by variation of the substitutent groups on the molecular core. The term "Bodipy dyes" and "Bodipy Dye Analogues" are used interchangeably herein.

fluorescence imaging may be assessed as described herein. Preferably, the compounds have the same or greater stability and fluorescence efficiency as the compounds described in the examples.

In a preferred embodiment, at least one of $R_1$-$R_6$ is alkyl or aryl, and, in a further preferred embodiment, at least one of $R_1$-$R_6$ is alkyl or phenyl. In a preferred embodiment, $R_1$, $R_3$, $R_4$ and $R_6$ are alkyl. In another preferred embodiment, $R_4$ is phenyl.

In a preferred embodiment, A is a halogen or aryl, and more preferably, A is fluorine or phenyl.

The dual modality imaging probe of the present invention may suitably be chosen so that it emits in the visible portion or Near-IR portion of the electromagnetic spectrum. In a preferred embodiment, the bodipy dye analog emits light in the Near-IR portion of the electromagnetic spectrum. One example of a near-IR Bodipy analog suitable for use in connection with the present invention is Compound 650-std, shown below, which may be radiolabelled using the methods described herein.

Compound 650-std

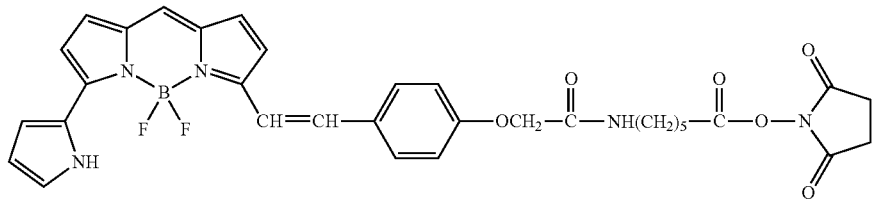

More specifically, one aspect of the present invention is directed to a dual modality imaging agents having the Formula I, including salts, hydrates and solvates thereof:

Formula I

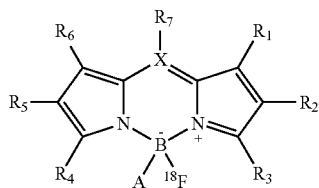

wherein $R_1$, $R_2$, $R_3$, $R_4$, $R_5$, $R_6$, and $R_7$ may be independently selected from the group consisting of hydrogen, halogen, hydroxy, alkoxy, nitro, substituted and unsubstituted amino, cycloalkyl, carboxy, carboxylic acids and esters thereof, cyano, haloalkyl, aryl, including phenyl and aminophenyl, azide, alkyne and heteroaryl;

X is selected from the group consisting of C and N;

A is selected from the group consisting of hydrogen, halogen, hydroxy, alkoxy, nitro, substituted and unsubstituted amino, alkyl, cycloalkyl, carboxy, carboxylic acids and esters thereof, cyano, haloalkyl, aryl, including phenyl and aminophenyl, and heteroaryl.

The substituents $R_1$-$R_7$, X and A should be chosen such that, when the compound is sufficiently stable, such that there is little, and preferably no, dissociation of the B-$^{18}$F bond in vivo, and when administered for fluorescence imaging, sufficiently high quantum yields for use in fluorescence imaging. Stability and suitability of the compounds for Another aspect of the present invention is directed to precursor bodipy analogues which may be rapidly and efficiently radiolabeled, preferably with $^{18}$F, for use as dual imaging agents. The precursor bodipy analogs of the present invention have the general Formula II, including salts, hydrates and solvates thereof:

Formula II

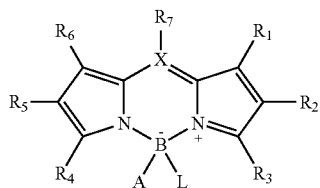

wherein $R_1$, $R_2$, $R_3$, $R_4$, $R_5$, $R_6$, and $R_7$ may be independently selected from the group consisting of hydrogen, halogen, hydroxy, alkoxy, nitro, substituted and unsubstituted amino, cycloalkyl, carboxy, carboxylic acids and esters thereof, cyano, haloalkyl, aryl, including phenyl and aminophenyl, azide, alkyne and heteroaryl;

X is selected from the group consisting of C and N;

A is selected from the group consisting of hydrogen, halogen, hydroxy, alkoxy, nitro, substituted and unsubstituted amino, alkyl, cycloalkyl, carboxy, carboxylic acids and esters thereof, cyano, haloalkyl, aryl, including phenyl and aminophenyl, and heteroaryl; and Leaving group, L, is selected from the group consisting of halogen, hydroxy, alkoxy, nitro, substituted and unsubstituted amino, cycloalkyl, carboxy, carboxylic acids and esters thereof, cyano, haloalkyl, aryl, including phenyl and aminophenyl, and heteroaryl. The leaving group is selected such that it can be rapidly and efficiently substituted with $^{18}F$ as described herein. In a preferred embodiment, the Leaving group L is halogen, such as fluoro or chloro, or a hydroxyl group.

In a preferred embodiment, at least one of $R_1$-$R_6$ is alkyl or aryl, and, in a further preferred embodiment, at least one of $R_1$-$R_6$ is alkyl or phenyl. In a preferred embodiment, $R_1$, $R_3$, $R_4$ and $R_6$ are alkyl. In another preferred embodiment, $R_4$ is phenyl.

In a preferred embodiment, A is a halogen or aryl, and more preferably, A is fluorine or phenyl.

Certain preferred embodiments of the precursors and dual imaging agents according to the present invention are shown in Formulas III-VI, and include salts, hydrates and solvates thereof:

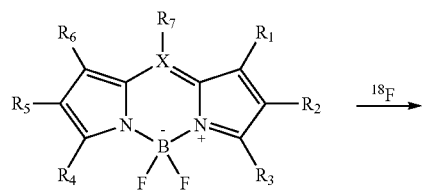

Formula III

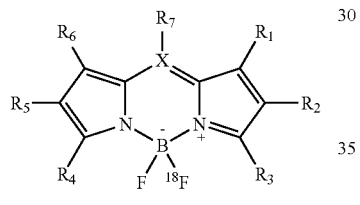

Formula IV

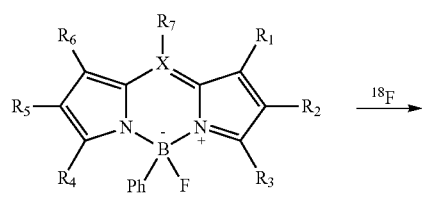

Formula V

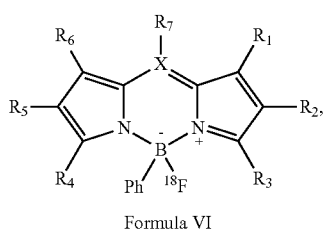

Formula VI wherein $R_1$-$R_7$, X and preferred embodiments are as described for Formula I.

Other preferred embodiments of the precursors of dual imaging agents according to the present invention are shown as Formula

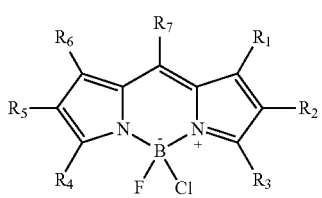

Formula VII

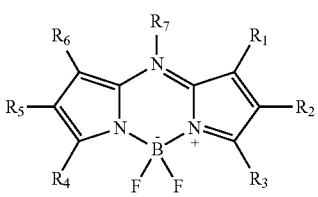

Formula VIII wherein $R_1$-$R_7$, and preferred embodiment are as described for Formula I.

In another embodiment of the present invention, another precursor dye compound and dual imaging agents include compounds of Formulas IX and X, and include salts, hydrates and solvates thereof.

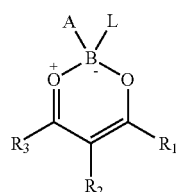

Formula IX

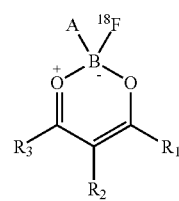

Formula X wherein $R_1$, $R_2$, and $R_3$, may be independently selected from the group consisting of hydrogen, halogen, hydroxy, alkoxy, nitro, substituted and unsubstituted amino, cycloalkyl, carboxy, carboxylic acids and esters thereof, cyano, haloalkyl, aryl, including phenyl and aminophenyl, azide, alkyne and heteroaryl;

A is selected from the group consisting of hydrogen, halogen, hydroxy, alkoxy, nitro, substituted and unsubstituted amino, alkyl, cycloalkyl, carboxy, carboxylic acids and esters thereof, cyano, haloalkyl, aryl, including phenyl and aminophenyl, and heteroaryl.

Leaving group, L, is selected from the group consisting of halogen, hydroxy, alkoxy, nitro, substituted and unsubstituted amino, cycloalkyl, carboxy, carboxylic acids and esters thereof, cyano, haloalkyl, aryl, including phenyl and aminophenyl, and heteroaryl. The leaving group is selected such that it can be rapidly and efficiently substituted with $^{18}F$ as described herein. In a preferred embodiment, the Leaving group L is halogen, such as fluoro or chloro, or a hydroxyl group.

The substituents $R_1$-$R_3$, X and A should be chosen such that, when the compound is sufficiently stable, such that there is little, and preferably no, dissociation of the B-$^{18}F$ bond in vivo, and when administered for fluorescence imaging, sufficiently high quantum yields for use in fluorescence imaging. Stability and suitability of the compounds for fluorescence imaging may be assessed as described herein. Preferably, the compounds have the same or greater stability and fluorescence efficiency as the compounds described in the examples.

In a preferred embodiment, A is a halogen or aryl, and more preferably, A is fluorine or phenyl.

In another embodiment of the present invention, other precursor dye compounds and dual imaging agents include compounds of Formulas XI and XII, and include salts, hydrates and solvates thereof.

Formula XI

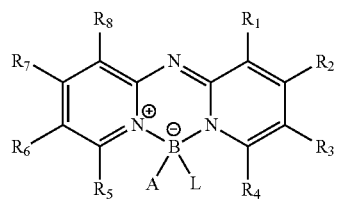

Formula XII

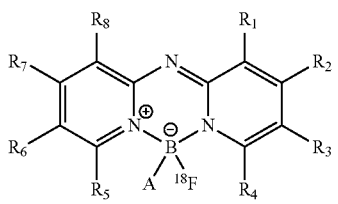

Formula XIII

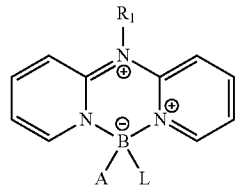

Formula XIV

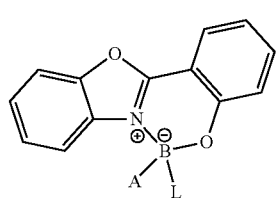

Formula XV

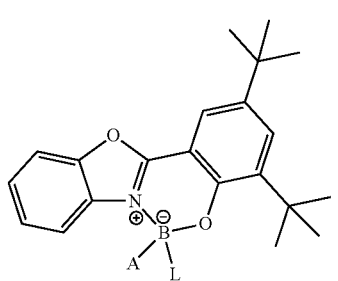

Formula XVI

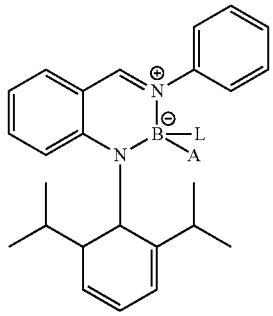

Formula XVII

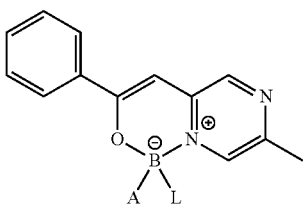

Formula XVIII

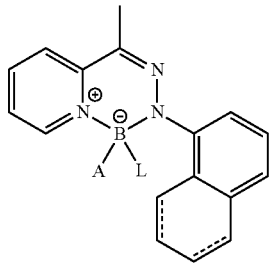

Formula XIX

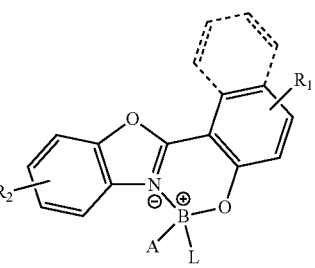

Formula XX

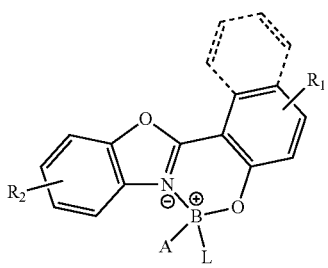

Formula XXI

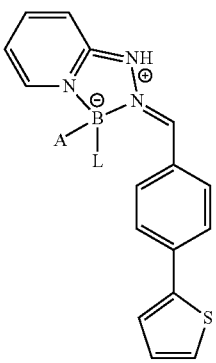

-continued

Formula XXII

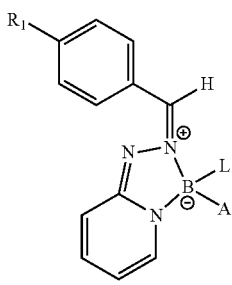

Wherein, for the foregoing compounds, $R_1$, $R_2$, $R_3$, $R_4$, $R_5$, $R_6$, $R_7$ and $R_8$ may be independently selected from the group consisting of hydrogen, halogen, hydroxy, alkoxy, nitro, substituted and unsubstituted amino, cycloalkyl, carboxy, carboxylic acids and esters thereof, cyano, haloalkyl, aryl, including phenyl and aminophenyl, azide, alkyne and heteroaryl;

A is selected from the group consisting of hydrogen, halogen, hydroxy, alkoxy, nitro, substituted and unsubstituted amino, alkyl, cycloalkyl, carboxy, carboxylic acids and esters thereof, cyano, haloalkyl, aryl, including phenyl and aminophenyl, and heteroaryl.

Leaving group, L, is selected from the group consisting of halogen, hydroxy, alkoxy, nitro, substituted and unsubstituted amino, cycloalkyl, carboxy, carboxylic acids and esters thereof, cyano, haloalkyl, aryl, including phenyl and aminophenyl, and heteroaryl. The leaving group is selected such that it can be rapidly and efficiently substituted with $^{18}F$ as described herein. In a preferred embodiment, the Leaving group L is halogen, such as fluoro or chloro, or a hydroxyl group.

The substituents $R_1$-$R_8$, X and A should be chosen such that, when the compound is sufficiently stable, such that there is little, and preferably no, dissociation of the B-$^{18}F$ bond in vivo, and when administered for fluorescence imaging, sufficiently high quantum yields for use in fluorescence imaging. Stability and suitability of the compounds for fluorescence imaging may be assessed as described herein. Preferably, the compounds have the same or greater stability and fluorescence efficiency as the compounds described in the examples.

In cases where compounds of Formula I through Formula XII are sufficiently basic or acidic to form stable nontoxic acid or base salts, the compounds may be generated and/or isolated as salts may be appropriate. Preferably, the salts are pharmaceutically acceptable salts. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including hydrochloride, sulfate, nitrate, bicarbonate, and carbonate salts.

The compounds of Formulas I through Formula X can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compounds' enantiomers and stereoisomers, that is, both the stereomerically pure form (e.g., geometrically pure, enantiomerically pure, or diastereomerically pure) and enantiomeric and stereoisomeric mixtures.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The nomenclature for specific compounds used herein generally assign a Compound numeral to a specific core, identifies the relevant leaving group, and whether it is radiolabelled. The abbreviations for these structures generally take the form "Compound [NO-L]$^{charge}$" or simply "[NO-L]$^{charge}$" as in the following preferred embodiments of the present invention:

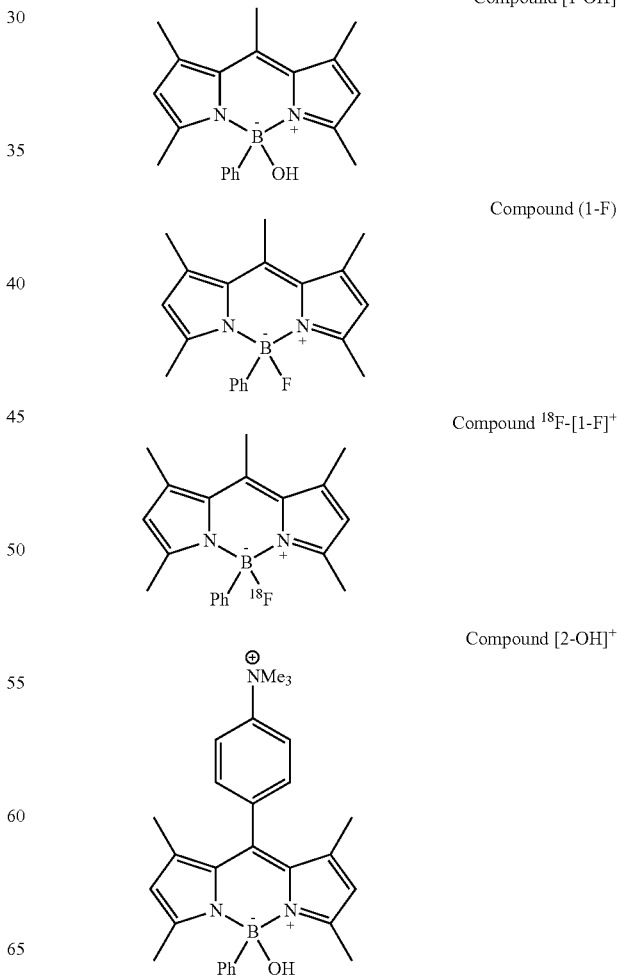

-continued
Compound [2-F]+
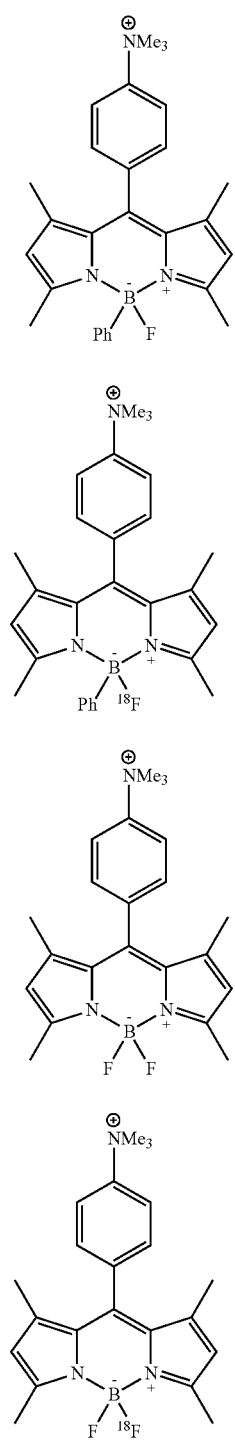
Compound 18F-[2-F]+
Compound [3-F]+
Compound 18F-[3-F]+
Compound [4-F]
-continued
Compound 18F-[4-F]
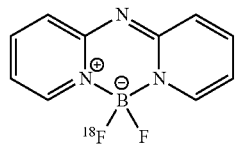
Compound [5-F]
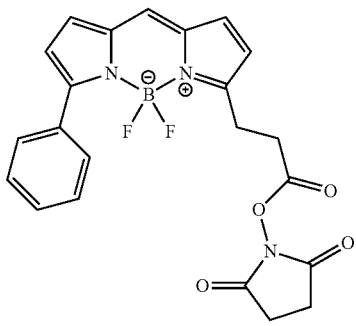
Compound 18F-[5-F]
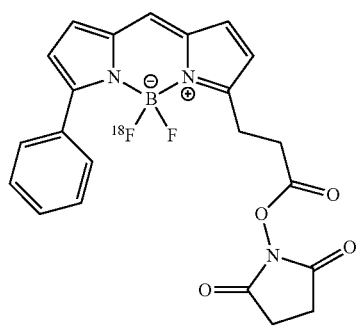
Compound [6-F]
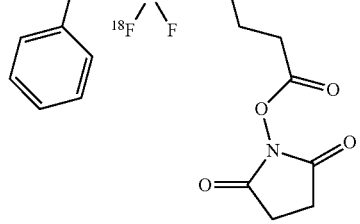
Compound [7-F]
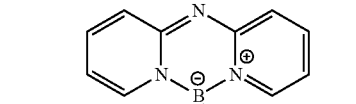
Compound [8-F]
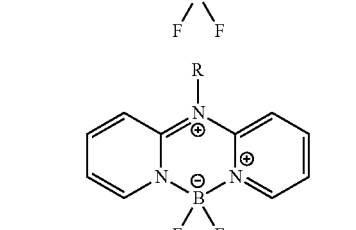
Compound [9-F]
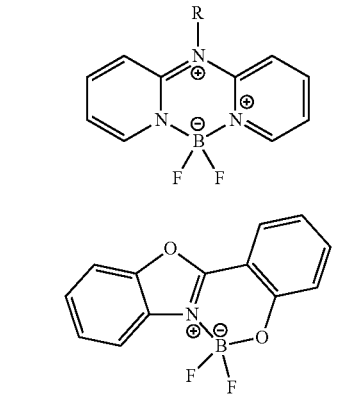

Compound [10-F]
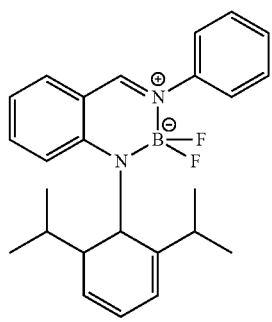
Compound [11-F]
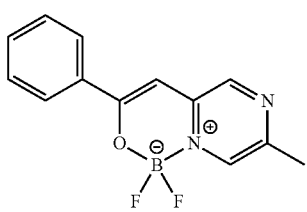
Compound [12-F]
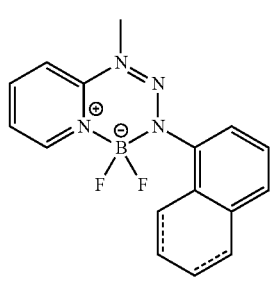
Compound [13-F]
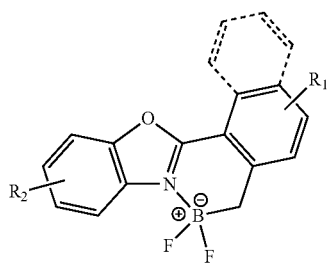
Compound [14-F]
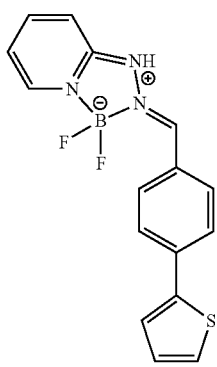
Compound [15-F]
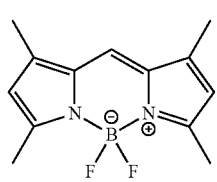
Compound [16-F]
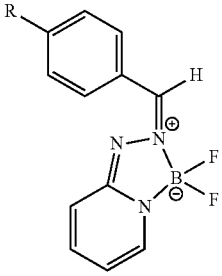
The dye analogs of the present invention may be made according to known methods, or by selection of the appropriate starting materials and reaction methodology as described in the examples and disclosure herein.

Scheme 1

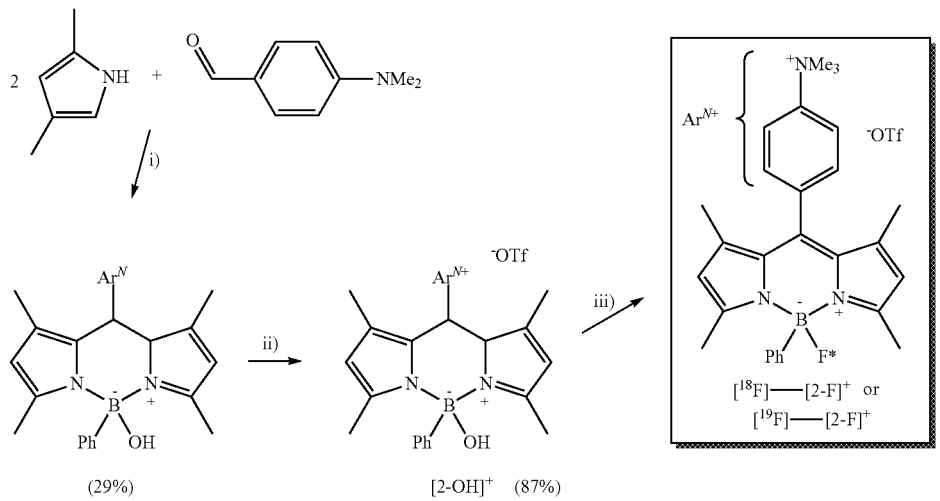

(29%)     [2-OH]⁺ (87%)

By way of example Scheme 1 shows the synthesis of bodipy analog compound Compound [2-OH]⁺. $Ar^N$=[4-$(Me_2N)$—$C_6H_4$]; $Ar^{N+}$=[4-$(Me_3N)$—$C_6H_4$]⁺. F*=$^{18}$F or $^{19}$F. Reagents and reaction conditions are as follows: i) p-chloranil, $Et_3N$, and $PhBCl_2$ in $CH_2Cl_2$ followed by aqueous workup; ii) MeOTf in $CH_2Cl_2$; iii) For [$^{19}$F]-[2-F]⁺: $KHF_2$, 0.95 M DCl in $MeOD/D_2O$ (1/1 vol.); For [$^{18}$F]-[2-F]⁺: $^{18}$F–/$KHF_2$, $H_2O$/MeOH, pH=2-3.

This reaction, which can be monitored by the appearance of a $^{19}$F NMR signal at −173 ppm, is complete in less than 2 minutes. The triflate salt of compound [2-F]⁺ has been fully characterized. The photophysical properties of this derivative are typical of other bodipy dyes. It features a broad absorption band at 506 nm and an emission band centered at 528 nm (Φ 14.3% in $CH_2Cl_2$). Encouraged by these synthetic and spectroscopic results, we investigated the radiofluorination of [2-OH]⁺ in aqueous solution.

Figure 2:
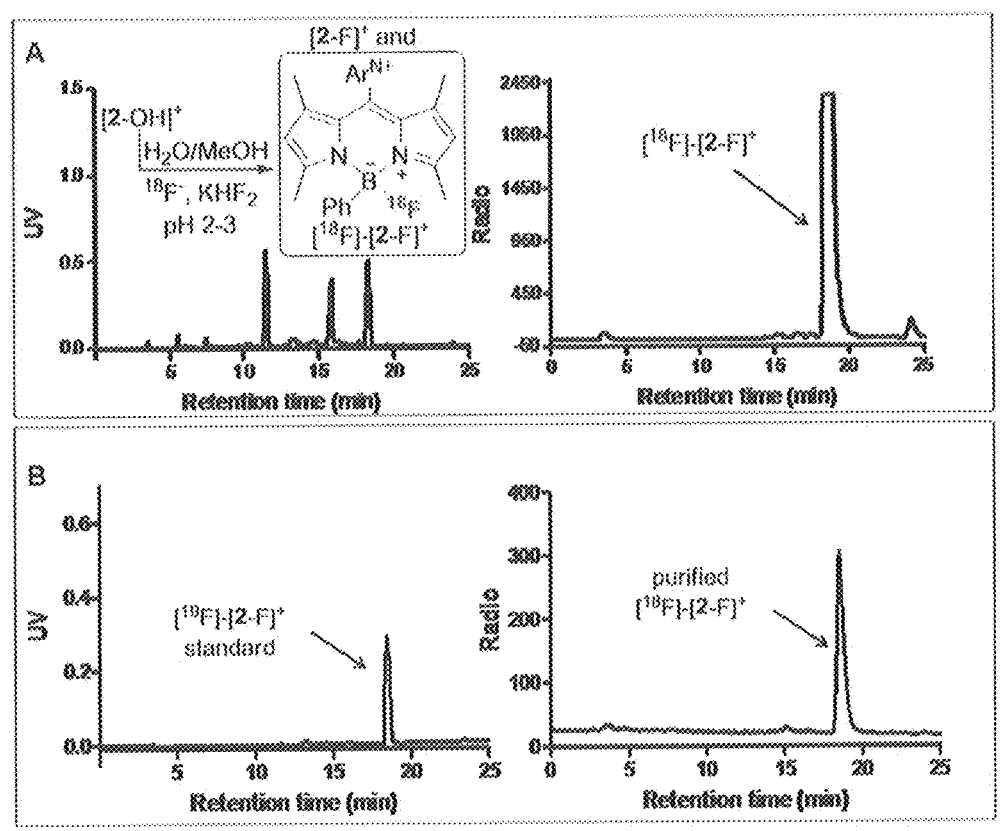
FIG. 2 shows (A) HPLC traces showing the formation of compound [$^{18}$F]-[2-F]$^+$; (B) HPLC trace obtained for the non-radiolabeled compound [2-F]$^+$ and the radio trace obtained for purified compound [$^{18}$F]-[2-F]$^+$.

One radiolabeling procedure is as follows: 30 mCi of [$^{18}$F]-fluoride (100 μL unfixed target water) was directly added to 5 μL of $KHF_2$ (0.1 mol/L). The mixture was heated at 70° C. for 10 min to ensure a complete homogenization. After cooling down to room temperature, compound [2-0H]⁺ (500 μg, 0.85 μmol in 100 μL MeOH) was added and the labeling was performed at room temperature for 15 min in the 2-3 pH range (Scheme 1). After dilution with 800 μL of water, the crude mixture was loaded onto a reverse phase HPLC and compound [$^{18/19}$F]-[2-F]⁺ was obtained in 22±3% yield (decay corrected, based on separation, n=4). The specific activity of the final product was calculated to be 25±4 mCi/μmol by comparing its UV absorption with the standard titration curve. The identity of compound [$^{18}$F]-[2-F]⁺ was confirmed by the co-injection with the non-radiolabeled standard (FIG. 2). To broaden the scope of our approach, we have also investigated the formation of compound [$^{18}$F]-[2-F]⁺ under no carrier added conditions. We first tested the reaction of compound [2-OH]⁺ with azeotropically dried [$^{18}$F]-TBAF in acetonitrile, which, however, did not afford any detectable yield of the target radiolabeled compound. The failure of this reaction to proceed can be assigned to the stability of the B—OH bond in compound [2-OH]⁺ as well as the presence of residual water in the [$^{18}$F]-TBAF and/or the acetonitrile.

To circumvent this difficulty, the reaction was repeated in the presence of an activating/water scrubbing agent such as TMSOTf. Compound [2-OH]⁺ (500 μg, 0.85 μmol in 100 μL MeCN) was pretreated with TMSOTf (20 eq.) and then subsequently mixed with a MeCN solution (100 μL) of azeotropically dried [18-F]-TBAF (10 mCi). This reaction, which was allowed to proceed for 5 min at 60° C., afforded [$^{18}$F]-[2-F]⁺ (specific activity≥ 1.4 Ci/μmol) in 61% yield as indicated by HPLC.

Figure 3:
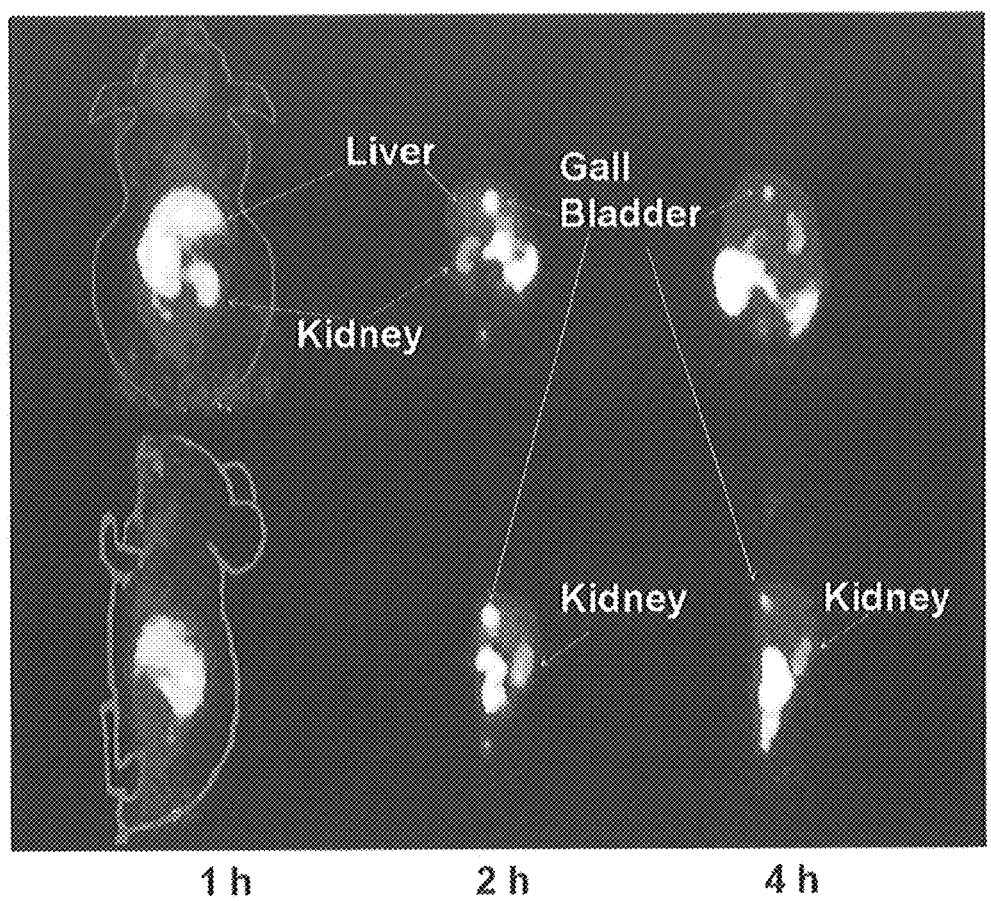
FIG. 3 shows PET images of a mouse injected with purified compound [$^{18}$F]-[2-F]$^+$. No detectable bone uptake is observed up to 4 h post-injection. All images shown are 2D projection instead of a single slice of the scan.

The stability of the resulting $^{18}$F—B compound is critical as free [$^{18}$F]-fluoride ions could bind to the bones giving rise to unwanted and interfering background signals.[14] The stability of compound [$^{18}$F]-[2-F]⁺ was first studied in PBS buffer at pH 7.5 over a period of several hours. HPLC analysis carried out at different time intervals indicated that the concentration of intact [$^{18}$F]-[2-F]⁺ decreased from about 99% after 1 h, to 97% after 3 h and 95% after 6 h thus pointing to the remarkable resistance of this derivative to hydrolysis at physiological pH (see Supporting Information). In order to validate the approach for in vivo PET imaging, [$^{18}$F]-[2-F]⁺ (prepared via the aqueous route) was injected into normal nude mice that were imaged using a microPET scanner 1 h, 2 h, and 4 h post injection. Bone uptake was not observed even at 4 h post injection, which indicates that the hydrolytic release of free [$^{18}$F]-fluoride from [$^{18}$F]-[2-F]⁺ is essentially negligible on the time scale of the $^{18}$F-nuclear decay (FIG. 3). More interestingly, accumulation of the radiolabeled probe primarily in the liver and kidneys but also in the gall bladder 2 h post injection was observed. Thus, although probe compound [$^{18}$F]-[2-F]⁺ lacks any specific targeting functionalities, its accumulation in these organs constitutes a normal phenomenon, in line with its hydrophobic and cationic nature.

Figures 4A, 4B:
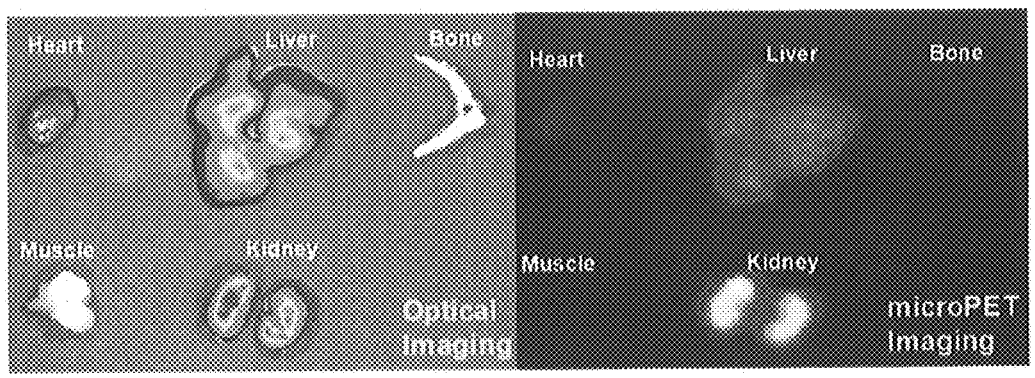
FIG. 4 shows representative ex vivo fluorescence (FIG. 4A) and microPET (FIG. 4B) imaging of dissected organs of a nude mouse. The animal was sacrificed after the microPET scan taken 4 h post injection.

The dual modality operation of the probe was confirmed. To this end, the animal was euthanized and selected organs harvested for ex vivo fluorescence and microPET imaging (FIG. 4). The fluorescence images were obtained by irradiation of the organs at λ=500 nm. This wavelength was chosen because it falls within the absorption band of [2-F]⁺ (see Supporting Information). The fluorescence image was reconstructed based on the emission intensity measured at λ=580±20 nm, a wavelength which is within the fluorescence band of [2-F]⁺ (see Supporting Information). As shown in FIG. 4, the ex vivo microPET and fluorescence imaging correlate extremely well with each other, showing accumulation of the probe in the liver and kidneys. These images are thus in perfect agreement with the in vivo PET studies which showed accumulations in the same organs. The heart and representative bones and muscles showed minimal uptake. Finally, the observed fluorescence from the liver and kidneys provide a further confirmation that $[2\text{-}F]^+$ is stable in vivo. Indirectly, these results indicate that $[2\text{-}F]^+$ is resistant to oxidative degradation reactions which can sometimes affect organoboron species.[15]

Imaging Compositions and Methods

Another aspect of the present invention is directed to pharmaceutical compositions for PET and/or Fluorescence Imaging and methods of PET and/or Fluorescence Imaging using the pharmaceutical compositions of the present invention.

The pharmaceutical compositions of the present invention generally comprise radiolabeld compositions according to one of Formulas I-XII, or a pharmaceutically acceptable salt thereof, dispersed or dissolved in a pharmaceutically acceptable carrier. The concentration the radiolabeled composition present in the application should be sufficiently high such that, when administered to the patient, the radiolabeled composition accumulates sufficiently in the tissue of interest to obtain adequate signal for PET and/or fluorescence imaging. The determination of the concentration and amount of the pharmaceutical composition to be administered is within the ordinary skill in the art.

The pharmaceutically acceptable carriers of the present invention may be the same or similar to those commonly used with PET and or fluorescence imaging. "Carriers" as used herein generally include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (e.g., glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin Another embodiment of the present invention is a method of PET and/or fluorescence imaging comprising administering to a patient in need thereof an effective amount of the radiolabelled compositions according to the present invention, and scanning the subject with at PET and/or fluorescence imaging device, wherein the detection of a PET or fluorescence signal corresponds to an image of a tissue of the subject. Here, an effective amount of the radiolabeled composition is an amount necessary to achieve sufficient accumulation in a tissue of interest to provide an adequate signal for PET and/or fluorescence imaging.

Fast and Efficient Radiolabelling of Bodipy Analogs and Boron-Fluorine Bonds with $^{18}F$ or $^{19}F$ As discussed and shown in the examples, the bodipy dye analogs of the present invention can be activated toward $[^{18}F]$-fluoride incorporation by several different methods. First, the bodipy dye analogs can be activated toward $[^{18}F]$-fluoride incorporation either under acidic conditions in aqueous solution or in organic solvents using the trimethylsilyl triflate (TMSOTf). These conditions are attractive because even simple bodipy dye analogs can be activated in the presence of $[^{18}F]$-fluoride ions toward substitution. One of the latent problems of these approaches is the fact that trimethylsilyl triflate also scavenges $[^{18}F]$-fluoride ions to form $[^{18}F]$-TMSF. This inherent side reaction is unwanted because of its negative effect on the specific activity of the bodipy dyes.

Another aspect of the present invention is a simple and ultra-efficient method for the $[^{18}F]$-fluoride incorporation into bodipy analog dyes thereby producing PET/fluorescence imaging agents comprising BODIPY dye analogs. The general and ultra-efficient $[^{18}F]$-labeling method for synthesizing $^{18}F$-labeled dyes according to the present invention comprises facilitating the $[^{18}F]$-fluoride substitution using Lewis acids. Specifically, bifunctional probe can be obtained through either $[^{19}F]$-fluoride/$[^{18}F]$-fluoride exchange reaction or the nucleophilic reaction on boron atom within the dye. The methods results in high yields. Preferably the methods used herein are applied to radiofluorination of bodipy dyes that emit in the NIR region for use in in vivo imaging of specific organs or diseases in the near future.

The radiolabelling method of the present invention generally comprises combining a compound comprising a B—F bond, preferably a Bodipy analog of the present invention with a $[^{18}F]/^{19}F\}$ Source Reagent in the presence of one or more Lewis Acids in a nonaqueous medium. The Bodipy analog is not particularly limited and may include any bodipy dye analog, including those of the present invention. The method, however, is not limited to Bodipy dye analogs. The radiolabelling method of the present invention may be applied, for instance, to the radiolabelling of B—F bonds in non-Bodipy dye analogs. The $[^{18}F]/[^{19}F]$ Source Reagent is generally a compound or reagent that is source of organic solvent-soluble fluoride ion. One suitable $[^{18}F]/^{19}F\}$ Source Reagent is [18F]-TBAF, Tetra-n-butylammonium fluoride, which is commercially available. Suitable Lewis Acids include SnCl4, $ZnCl_2$, $GaCl_3$, $FeCl_3$, $TiCl_4$, $AlCl_3$, $AlF_3$, $InCl_3$, $SnCl_2$, $ScCl_3$, $ZrCl_4$, $CrCl_3$, $CoCl_3$, FeCl, $CoCl_2$, $NiCl_2$, $CuCl_2$, $CH_3CO^+$, $Cu^+$, $Au^+$, $Hg^{2+}$, $Pb^{2+}$, $ZnBr_2$, $ZnF_2$, $ZnI_2$, $ZnMe_2$, $ZnEt_2$, $ZnPh_2$. Although the reaction may usually be carried out with a single Lewis Acid, it may be advantageous to use a combination of suitable Lewis Acid, such as a combination of SnCl$_4$ and ZnCl$_2$, which assists in the promoting high yields in bodipy dyes prone to degradation. An especially preferred Lewis acid for use in the present invention is SnCl$_4$.

One aspect of the present inventions is the discovery that Lewis acids, and especially SnCl$^4$, can greatly facilitate the $^{18}$F/$^{19}$F exchange on boron-fluoride bond as shown in Table 1.

Figure 11:
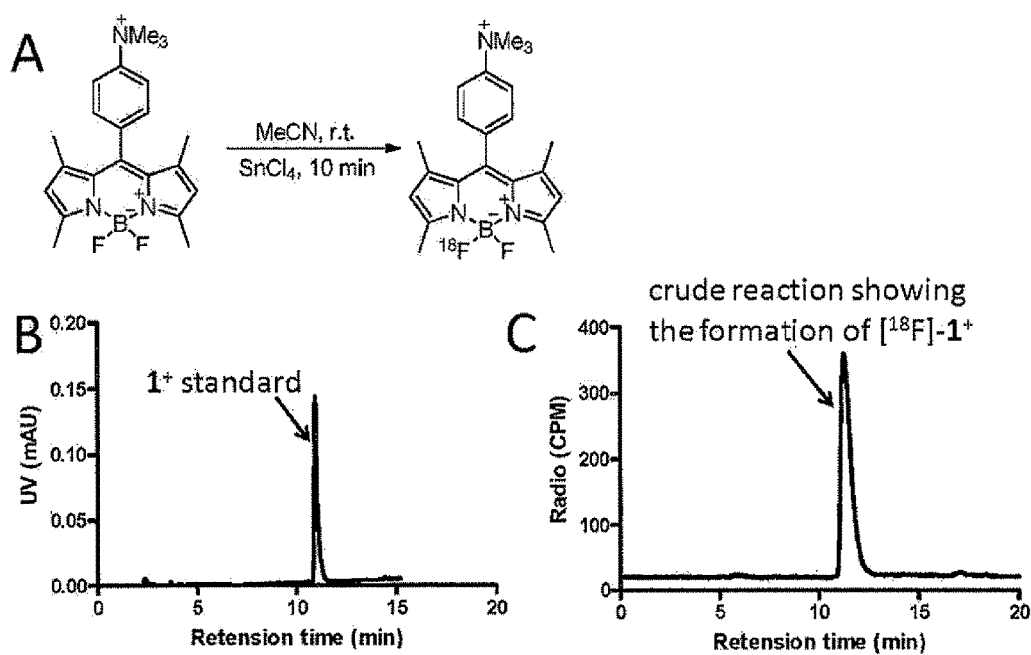
FIG. 11 shows (A) The synthetic scheme for [$^{18}$F]-[3-F]$^+$. (B) UV trace of compound [3-F]$^+$ as the standard reference. (C) Crude radio-HPLC profile for $^{18}$F labeling of [3-F]$^+$.

ZnCl$_2$ could successfully help the $^{18}$F labeling, but with lower yield at room temperature (Table 1, entry 4, 8). Although the labeling yield was increased at elevated temperature, a hydrophobic side product was produced during the reaction. In contrast, SnCl$_4$ turned out to be an ultra-effective agent for this process. The $^{18}$F labeling could be performed in almost quantitative yield at various conditions. The final product could be obtained with more than 1 Ci/μmol specific activity. As shown in entry 12 and 13, AlCl$_3$ lead to low labeling yield, which may be attributed to the strong Al—F bond formation as it could make the fluoride unavailable to the labeling reaction.[9] Although AlF$_3$ may avoid the limitation, the additional fluoride source may decrease the labeling yield. In summary, SnCl$_4$ is an ultra efficient additive for $^{18}$F labeling of BODIPY dye analogs. The representative crude HPLC profile of the labeling is shown in FIG. 11.

TABLE 1

Radiosynthetic results
3→$^{18}$F-3

| Entry | 1 (μg) | [$^{18}$F]-Activity (mCi) | Additive | Temp (° C.) | Solvent | Yield |
|---|---|---|---|---|---|---|
| 1 | 200 | 10 | H$^+$ | 37 | H$_2$O | <2 |
| 2 | 200 | 10 | TMSOTf | 37 | MeCN | 25 |
| 3 | 200 | 10 | SnCl$_4$ | 25 | MeCN/DMSO | 65 |
| 4 | 200 | 10 | ZnCl$_2$ | 25 | MeCN/DMSO | <2 |
| 5 | 200 | 10 | SnCl$_4$ | 25 | MeCN | >95 |
| 6 | 20 | 10 | SnCl$_4$ | 25 | MeCN | >95 |
| 7 | 20 | 10 | ZnCl$_2$ | 25 | MeCN | 15 |
| 8 | 20 | 10 | ZnCl$_2$ | 40 | MeCN | 30 |
| 9 | 20 | 10 | ZnCl$_2$ | 75 | MeCN | 45 |
| 10 | 20 | 100 | SnCl$_4$ | 25 | MeCN | >92 |
| 11 | 20 | 10 | AlCl$_3$ | 25 | MeCN | <2 |
| 12 | 20 | 10 | AlCl$_3$ | 75 | MeCN | <2 |

Figure 12:
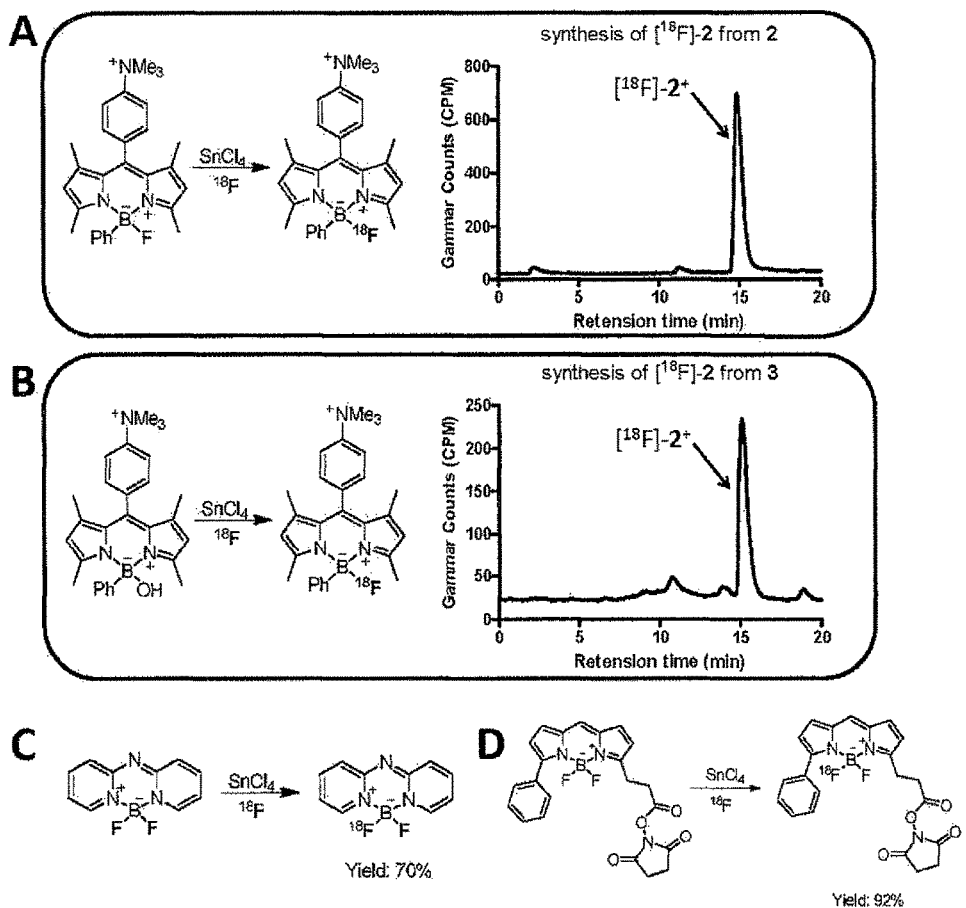
FIG. 12 shows the crude radio-HPLC traces showing the efficient formation of compound [$^{18}$F]-[2-F]$^+$ from (A) compound [2-F]$^+$ and (B) compound [2-OH]$^+$ using $SnCl_4$ as an additive. (C) [$^{18}$F]-fluorination of synthesized difluoroboron compound [4-F]$^+$. (D) [$^{18}$F]-fluorination of BODIPY NHS ester compound [5-F]$^+$.

The addition of SnCl$_4$ also facilitates the $^{18}$F/$^{19}$F exchange, including the $^{18}$F labeling, of mono-fluorinated BODIPY analogs, including compound [2-F] (FIG. 12A). $^{18}$F labeling could be achieved almost in quantitative yield. The method can be applied to the $^{18}$F labeling of other dyes containing monofluoroboron bond.

The addition of SnCl$_4$ also facilitates the $^{18}$F/$^{19}$F exchange, including the $^{18}$F labeling, of Bodipy dye analogs with no fluoride in the dye, such as compound Compound [2-OH], but with an exchangeable hydroxide group (FIG. 12B). The labeling yield was found to be more than 80%. This example demonstrated that Lewis acids could also facilitate the $^{18}$F labeling reactions through nucleophilic attack on boron atom, in addition to the above demonstrated fluoride exchange reaction. The method was also tested in a non-bodipy dye with B—F bond. As shown in FIG. 12C, the $^{18}$F labeled product was obtained with 60% labeling yield. These examples clearly demonstrated that the SnCl$_4$ method provides a general and robust way to $^{18}$F labeling of dyes containing B—F bond. To demonstrate the biological application, we used this method to label a commercially available BODIPY NHS ester, compound [5-F]. We achieved 92% yield and the $^{18}$F/$^{19}$F ester readily conjugates with amino-containing bioligand.

A study of the stability of [$^{18}$F]-[3-F]$^+$ in PBS buffer at pH 7.5 over a period of several hours was done. The HPLC profile indicated that the intact [$^{18}$F]-[3-F]$^+$ maintained at more than 97% after 6 h incubation, thus indicating the remarkable resistance of this derivative to hydrolysis at physiological pH (supporting information).

Figure 13:
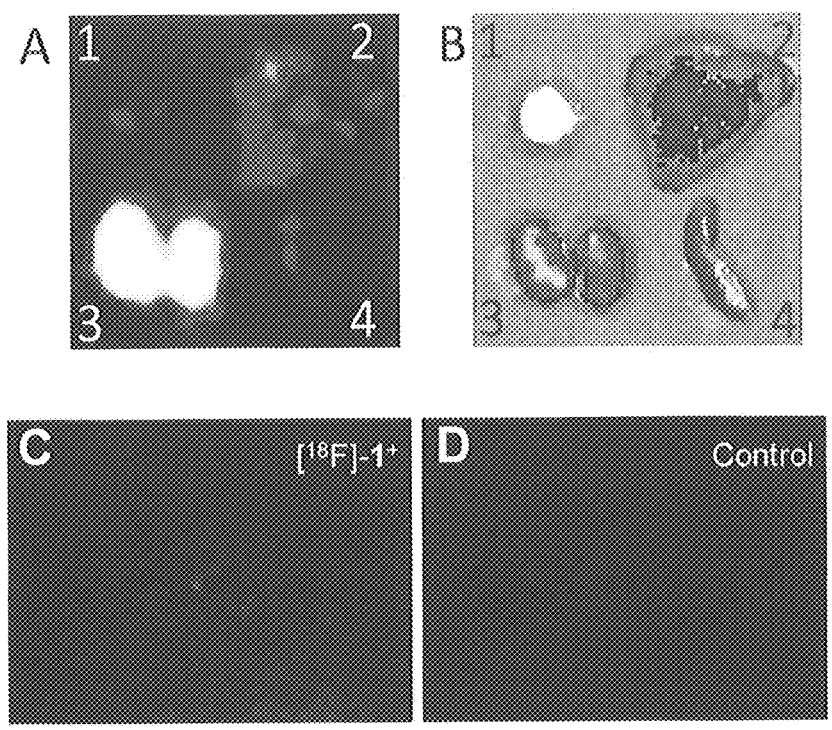
FIG. 13 shows representative ex vivo microPET (A) and fluorescence (B) imaging of dissected organs of a nude mouse. The observation of compound [$^{18}$F]-3$^+$ in mouse kidneys (C) and the kidney of control animal (D). The animal was sacrificed after the microPET scan 3 h post injection. 1. Muscle. 2. Liver. 3. Kidneys. 4. Spleen.
Figure 14:
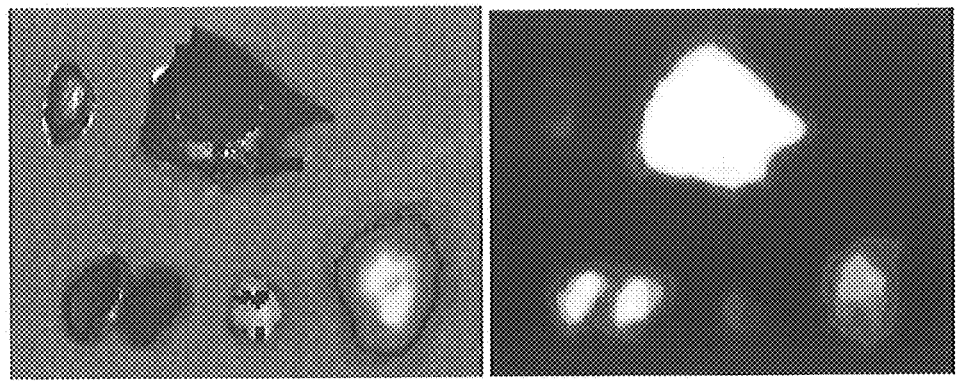
FIG. 14 shows PET and Optical Fluorescence scans of 1. Heart 2. Liver 3. Kidneys 4. Muscle 5. from a mouse model injected with Compound $^{18}$F-[5-F]-RGD.

[$^{18}$F]-[3-F]$^+$ was injected into normal nude mice that were imaged using a microPET scanner at 30 min, 1 h, and 3 h post injection in order to further validate our compound and demonstrate its potential for in vivo PET imaging. Obvious bone uptake even at 3 h post injection was not observed, which is consistent with the reported high stability of BODIPY dyes. Next, the dual modality potential of the probe was confirmed. The animal was euthanized and liver, kidneys and muscle were harvested for ex vivo PET/fluorescence imaging. As shown in FIG. 13, the ex vivo microPET and fluorescence imaging correlate very well with each other. We also sectioned the kidney and observed the BODIPY fluorescent signal under microscope. A prominent fluorescent signal was observed under microscope when the mice were injected [$^{18}$F]-[3-F]$^+$. In comparison, minimal signal was observed in the kidney of control mouse.

Thus, another aspect of the present invention is a method of studying the localization of PET probes within the tissue using fluorescent microscope. In another way, it should also allow the hits based on fluorescent microscope screening to be readily translated into PET probes for clinical usage, as they are exactly the same molecule.

The fluoride exchange reaction was also studied under acidic condition or in the presence of TMSOTf. Under acidic conditions, significant amount of compound [3-F] was decomposed. The labeling yield was less than 2%. In organic solvent, the labeling yield was higher. Compound $^{18}$F-3 could be obtained in 25% labeling yield. However, the reaction conditions need to be controlled carefully to avoid the production of TMS$^{18}$F as we mentioned previously.

Although we could obtain compound [$^{18}$F]-[3-F] through fluoride exchange reactions, the labeling yield is moderate and significant amount of the dye is decomposed during the synthesis.

Bodipy Dye Analog-Targeting Moiety Conjugates

In order to increase the biologic uptake or to increase the tissue specificity of the dual imaging probes of the present invention, the bodipy dye analogs of the present invention may be conjugated to targeting moieties to form Bodipy Dye-Targeting Moiety conjugates. The nature of the targeting moiety is not particularly limited so long as (1) the targeting moiety retains its retains a significant portions of its activity when linked to the Bodipy dye analog and (2) the bodipy dye analog imaging probe significantly retains it imaging capabilities when conjugated to the targeting moiety. One suitable targeting moiety of the present invention are RGD peptide, including cyclic-RGD peptides.

A radiolabelled dual imaging probe conjugated to a targeting moiety may be synthesized using at least two different methods. In first method, the bodipy dye analog is first radiolabelled using the Lewis Acid based methods of the present invention, and then the radiolabeled Bodipy dye analog is conjugated to a targeting moiety. Alternatively, and preferably, the bodipy dye analog is first conjugated to a targeting moiety and then the Bodipy dye analog/Targeting moiety conjugate is radiolabeled preferably using the Lewis Acid based methods of the present invention.

Suitable targeting moiety of the present invention include compound RGD1 and compound PRGD2

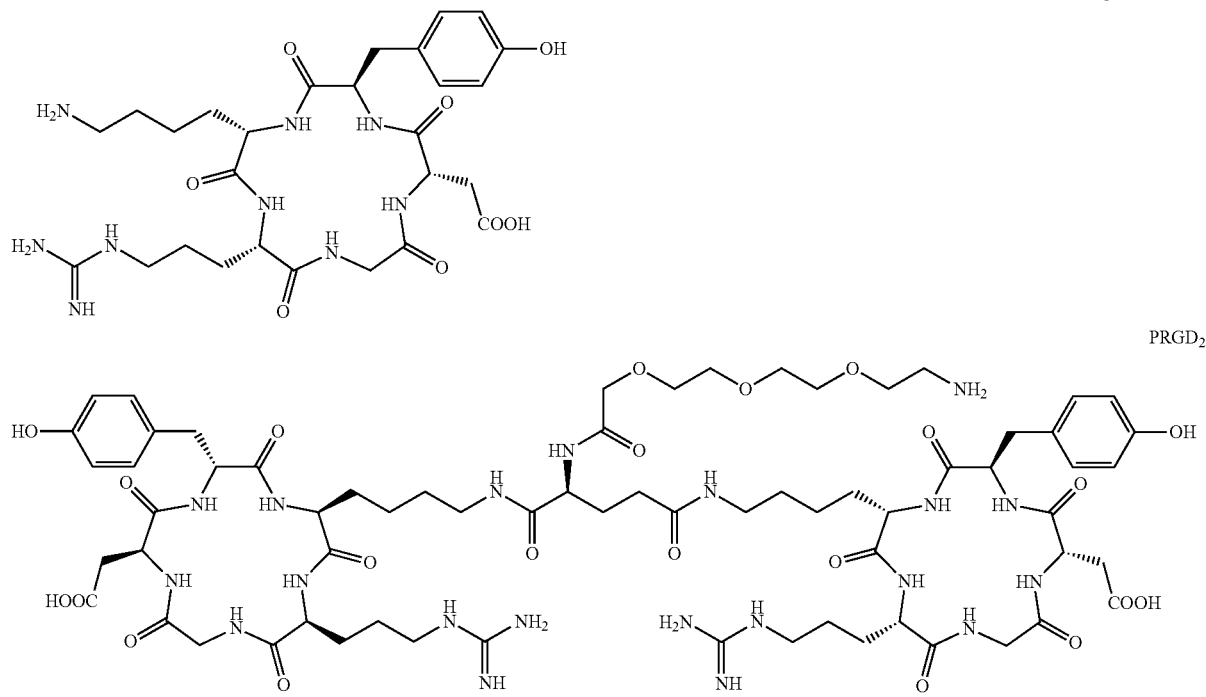

Compound RGD1

PRGD2

In an exemplary embodiment of one aspect of the present invention as shown in Scheme 2, a bodipy dye analog, compound [5-F], is first radiolabelled with $^{18}F$ and then conjugated to the RGD1 moiety.

As shown in Scheme 3, the Bodipy analog-Targeting Moiety Conjugate of PRGD2 may be synthesized in an analogous manner.

Scheme 2

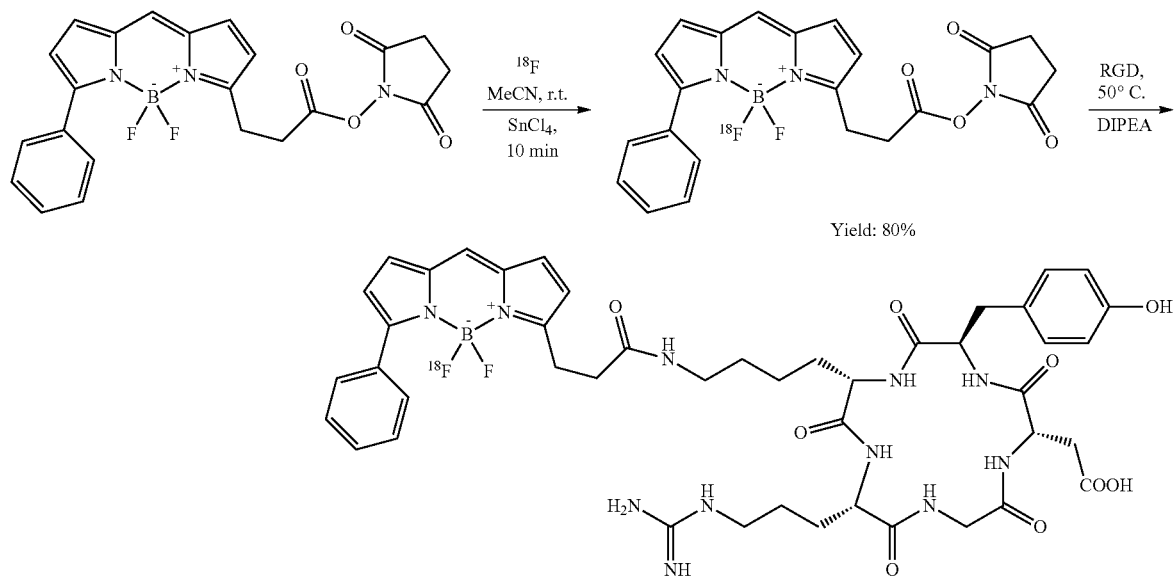

Yield: 80%

Yield: 82%

Scheme 3
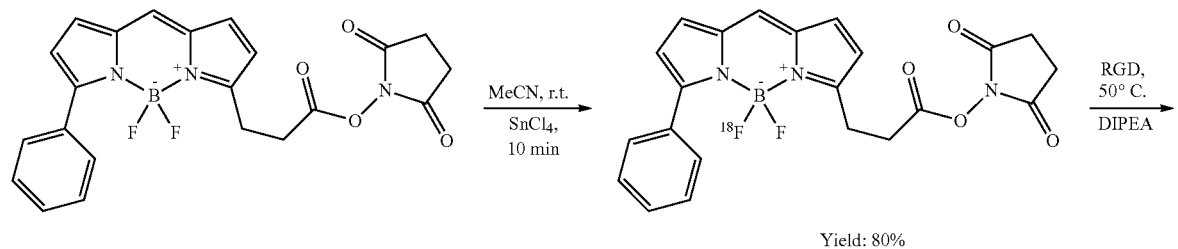
Yield: 80%
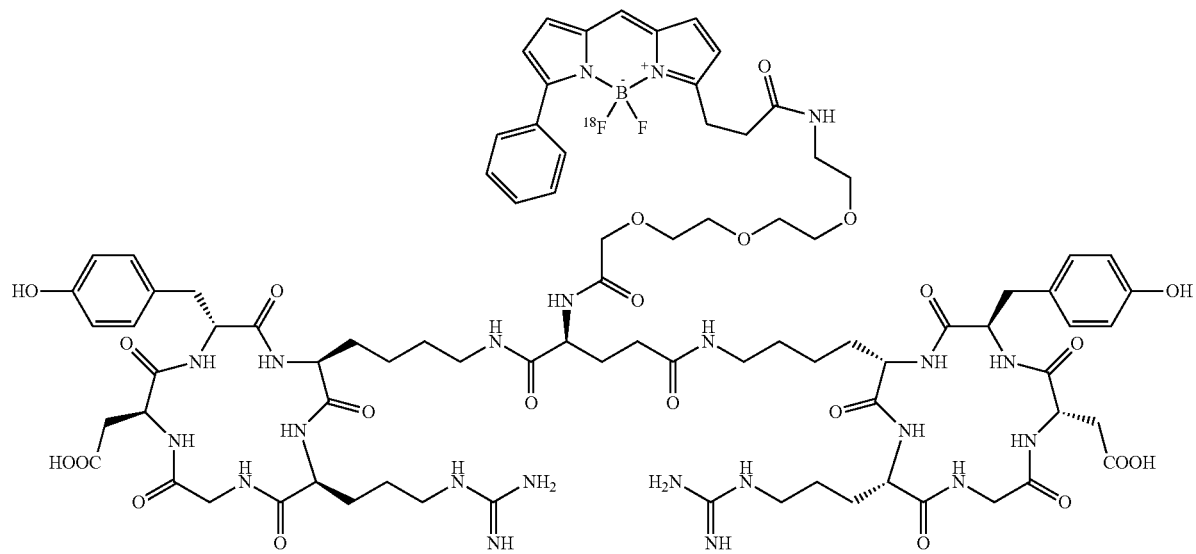
Yield: 65%
Alternatively, as shown in Scheme 4 and Scheme 5, the unlabelled bodipy dye analog-Targeting Moiety may be prepared first and then radiolabeled directly.
Scheme 4
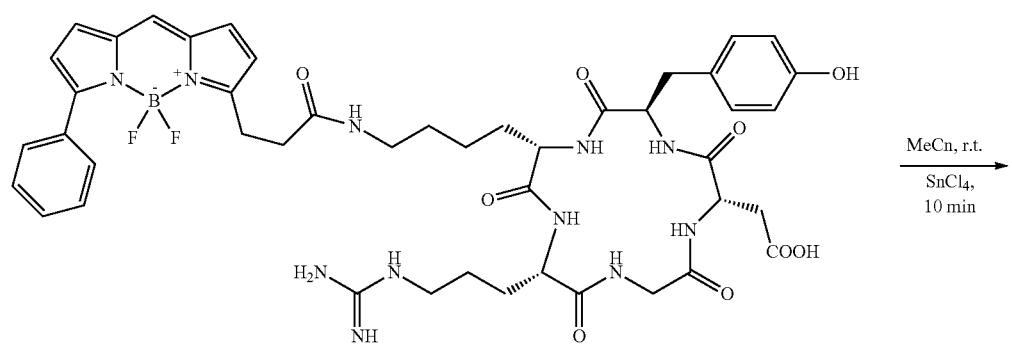

27
28
-continued
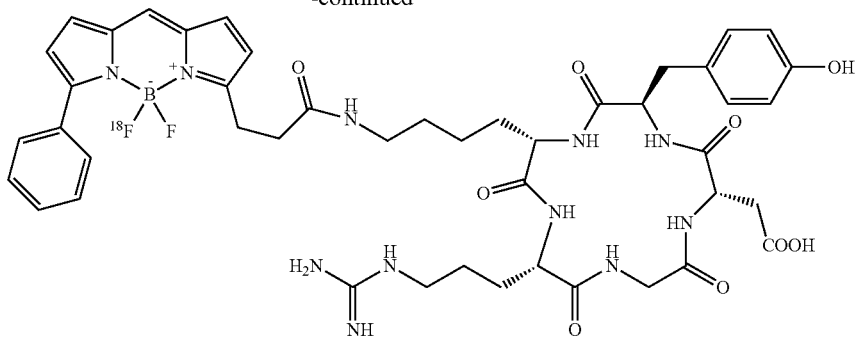
25 % yield
Compound ¹⁸F—[5-F]—RGD
Scheme 5
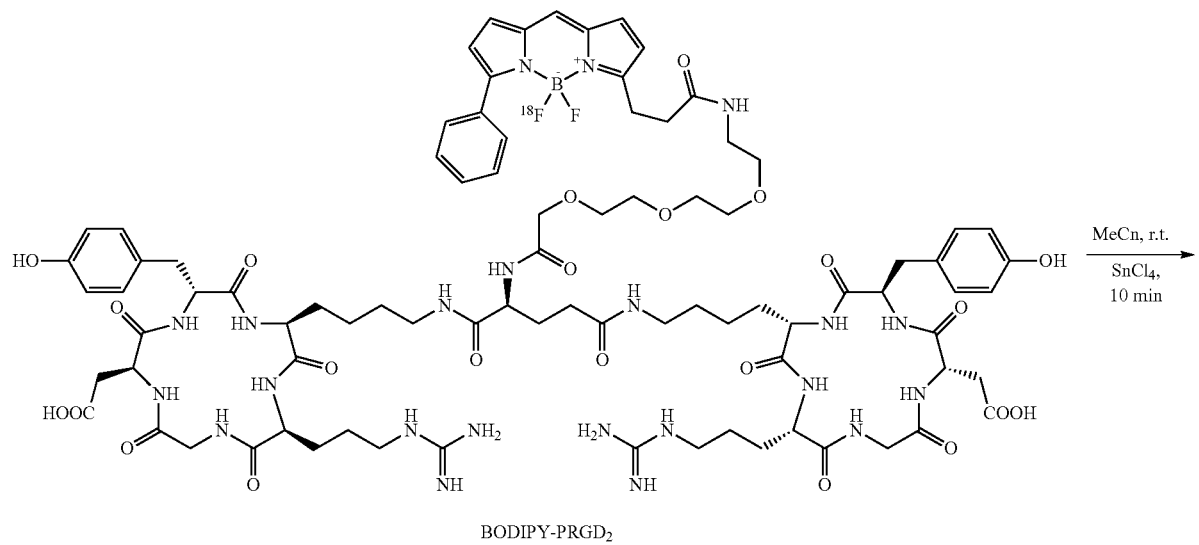
BODIPY-PRGD₂

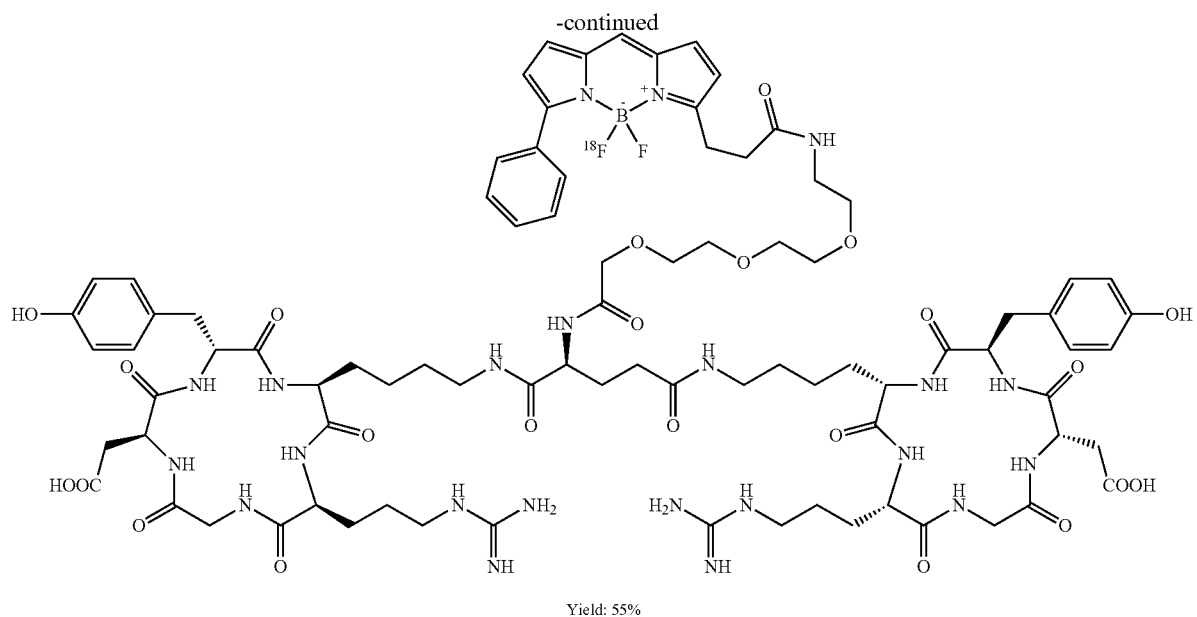

Yield: 55%

As would be evident to those skilled in the art, the bodipy dye analog, Compound 5, shown in Schemes 2-5 could be substituted with other bodipy dye analogs described herein so long as a suitable linking species is retained for conjugation of to the Targeting moiety. Also, as would be evident to those of ordinary skill, the Targeting Moiety shown, other RGD or targeting moieties could be substituted for the Targeting Moieties of Schemes 2-5.

EXAMPLES

The following examples are provided in order to demonstrate and further illustrate certain embodiments and aspects of the present invention and are not to be construed as limiting the scope thereof.

Example 1

Synthetic Methods and Materials

General Considerations.

4-dimethylaminobenzaldehyde, p-chloranil, and phenylboron dichloride were purchased from Aldrich. 2,4-dimethylpyrrole was purchased from TCI. All preparations were carried out under an atmosphere of dry $N_2$ employing either a glove box or standard Schlenk techniques. Solvents were dried by passing through an alumina column ($CH_2Cl_2$) or refluxing under $N_2$ over Na/K ($Et_3N$). NMR spectra were recorded on a Varian Unity Inova 400 NMR and an Inova 500 NMR spectrometer at ambient temperature. Chemical shifts are given in ppm, and are referenced to residual $^1H$ and $^{13}C$ solvent signals and external neat $BF_3$-$Et_2O$ for $^{11}B$ and $^{19}F$. Electrospray mass spectra were acquired on a MDS Sciex API QStar Pulsar. The spray voltage was 4.5 kV. All spectra were obtained in positive mode from $CH_3CN$. HPLC analyses were carried out on a analytical reversed-phase high performance liquid chromatography (HPLC) system equipped with a dual UV absorbance detector (Waters 2487) using a phenomenex C18 RP (250×4.6 mm 5 micron). The flow was 1 mL/min, with the mobile phase starting from 95% solvent A (0.1% TFA in water) and 5% solvent B (0.1% TFA in acetonitrile) (0-2 min), followed by a gradient mobile phase to 5% solvent A and 95% solvent B at 22 min. The radioactivity was detected by a model of Ludlum 2200 single-channel radiation detector. The stability study was performed using the same HPLC condition.

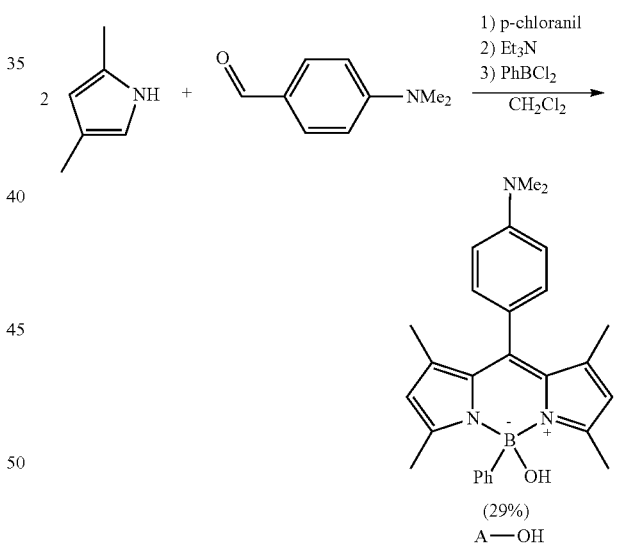

Synthesis of 10-dimethyl-aminophenyl-5-hydroxyl-5-phenyl-1,3,7,9-tetramethyl-5H-dipyrrolo[1,2-c:1',2'-f][1,3,2]diazaborinin-4-ium-5-uide Compound [A-OH]

2,4-dimethylpyrrole (298 mg, 3.13 mmol) was dissolved in 300 mL of dichloromethane. To this solution, 4-dimethylaminobenzaldehyde (381 mg, 2.55 mmol) was added two drops of trifluoroacetic acid. The resulting solution became dark red, and was stirred for three hours at room temperature. The red solution was then treated with p-chloranil (491 mg, 2.00 mmol) in dichloromethane (250 mL) and stirred for 15 minutes. Dry triethylamine (1.0 mL, 13.6 mmol) was then added followed by dropwise addition of phenylboron dichloride (1.49 g, 9.38 mmol) in Et$_2$O (10 mL) which resulted in a green fluorescent solution. The solution was stirred overnight then quenched with water (2×300 mL). After each wash the organic layer was separated and then dried over MgSO$_4$. The solvent was removed in vacuo and then chromatographed on silica eluting with chloroform until all of the green fluorescent material had eluted (followed using a hand-held UV lamp). The solvent was again removed under reduced pressure. This residue was subjected to column chromatography over a small column of silica gel using toluene:hexanes (80:20 v/v) as the eluent (followed using a UV lamp). The fractions with the green fluorescence were combined and the solvent removed to afford the desired product compound [A-OH] as an orange solid (310 mg, 29% yield). $^1$H NMR (399.59 MHz; CDCl$_3$): δ 1.49 (s, 6H, dipyrrin-CH$_3$), 2.17 (s, OH, dipyrrin-CH$_3$), 3.02 (s, 6H, N—CH$_3$), 5.85 (s, 2H, dipyrrin-CH), 6.80 (t, 2H, $^3$J=8.5 Hz, phenyl-CH), 7.09-7.25 (m, 5H, phenyl-CH), 7.42 (d, 2H, $^3$J=7.0 Hz, phenyl-CH). $^{13}$C{$^1$H} NMR (100.45 MHz, CDCl$_3$): δ 16.36, 16.73, 17.74, 122.60, 126.47, 126.93, 131.45, 133.29, 140.24, 141.38, 154.73. B—C peak not observed. $^{11}$B{$^1$H} NMR (128.20 MHz, CDCl$_3$): δ 2.53.

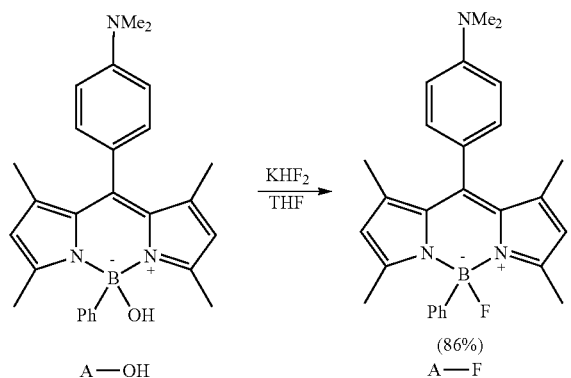

Synthesis of 10-dimethyl-aminophenyl-5-fluoro-5-phenyl-1,3,7,9-tetramethyl-5H-dipyrrolo[1,2-c:1',2'-f][1,3,2]diazaborinin-4-ium-5-uide Compound [A-F]

A THF (5 mL) solution of A-OH (100 mg, 0.236 mmol) was treated with KHF$_2$ (111 mg, 1.417 mmol) and stirred for 24 hours. The reaction mixture was then quenched with water (10 mL) and extracted with dichloromethane (3×5 mL). The organic layers were combined, dried over MgSO$_4$, and filtered. The solvent was removed under reduced pressure and the residue was recrystallized at −40° C. from EtOAc (5 mL) to afford the desired product, compound [A-F] as a bright orange crystalline solid (86 mg, 86% yield). $^1$H NMR (399.59 MHz, CDCl$_3$): δ 1.49 (s, 6H, dipyrrin-CH$_3$), 2.16 (s, 6H, dipyrrin-CH$_3$), 3.02 (s, 6H, N—CH$_3$), 5.85 (s, 2H, dipyrrin-CH), 6.80 (t, 2H, $^3$J=8.5 Hz, phenyl-CH), 7.09-7.25 (m, 5H, phenyl-CH), 7.42 (d, 2H, $^3$J=7.0 Hz, phenyl-CH). $^{13}$C{$^1$H} NMR (100.45 MHz, CDCl$_3$): δ 16.36, 16.73, 17.74, 122.60, 126.47, 126.93, 131.45, 133.29, 140.24, 141.38, 154.73. B—C peak not observed. $^{19}$F{$^1$H} NMR (375.97 MHz, CDCl$_3$): δ −173.9. $^{11}$B{$^1$H} NMR (128.20 MHz, CDCl$_3$): δ 2.51.

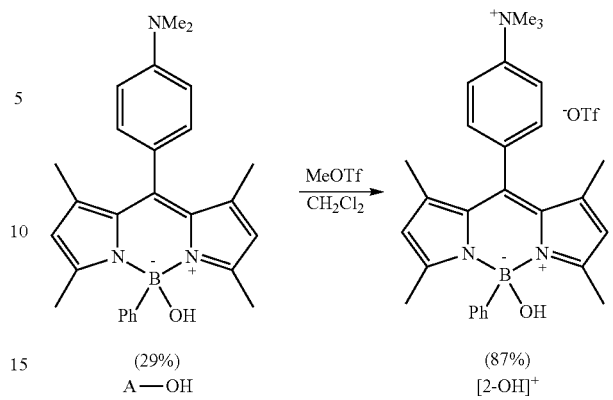

Synthesis of [2-OH][OTf]

To a dichloromethane (5 mL) solution of compound [A-OH] (80 mg, 0.189 mmol) was added a dichloromethane (2 mL) solution of methyl trifluoromethanesulfonate (19.2 mg, 0.246 mmol) dropwise. The formation of an orange precipitate was observed after stirring for 15 min. This solid was collected by filtration and washed with hexane (20 mL) to yield a pure sample of compound [2-OH][OTf] (97 mg, 87%). $^1$H NMR (499.43 MHz, CD$_3$CN): δ 1.38 (s, 6H, dipyrrin-CH$_3$), 2.20 (s, 6H, dipyrrin-CH$_3$), 3.60 (s, 9H, N—CH$_3$), 5.96 (s, 2H, dipyrrin-CH), 7.11 (t, 1H, $^3$J=7.2 Hz, phenyl-CH), 7.18 (t, 2H, $^3$J=7.1 Hz, phenyl-CH), 7.41 (d, 2H, $^3$J=7.7 Hz, phenyl-CH), 7.71 (dd, 2H, $^3$J=38.9, 8.1 Hz, phenyl-CH), 7.93 (t, 2H, $^3$J=10.1 Hz, phenyl-CH). $^{13}$C{$^1$H} NMR (125.59 MHz, CD$_3$CN): δ 15.0, 15.9, 58.2, 121.9, 122.0, 122.1, 126.8, 127.8, 131.7, 132.8, 132.9, 133.0, 139.2, 140.5, 141.6, 148.3, 156.8. $^{18}$F{$^1$H} NMR (469.87 MHz, CD$_3$CN): δ −78.1. $^{11}$B{$^1$H} NMR (128.20 MHz, CD$_3$CN): δ 2.70. HRMS (ESI$^+$) calcd for [2-OH]$^+$ (C$_{28}$H$_{33}$BN$_3$O$^+$): 438.2711. found: 438.2735.

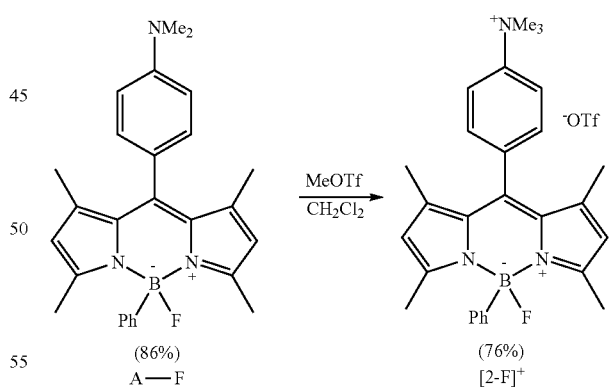

Synthesis of Compound [2-F][OTf]

To a dichloromethane (5 mL) solution of A-F (63 mg, 0.148 mmol) was added a dichloromethane (2 mL) solution of methyl trifluoromethanesulfonate (15 mg, 0.193 mmol) dropwise. The formation of an orange precipitate was observed after stirring for 15 min. This solid was collected by filtration and washed with hexane (20 mL) to yield a pure sample of Compound [2-F][OTf] (66 mg, 76%). $^1$H NMR (499.43 MHz, MeOD): δ 1.42 (s, 6H, dipyrrin-$CH_3$), 2.14 (s, 6H, dipyrrin-$CH_3$), 3.76 (s, 9H, N—$CH_3$), 5.99 (s, 2H, dipyrrin-CH), 7.12 (t, 1H, $^3J$=7.4 Hz, phenyl-CH), 7.18 (t, 2H, $^3J$=6.9 Hz, phenyl-CH), 7.36 (d, 2H, $^3J$=7.0 Hz, phenyl-CH), 7.75 (dd, 2H, $^3J$=31.0, 8.5 Hz, phenyl-CH), 8.15 (t, 2H, $^3J$=10.2 Hz, phenyl-CH). $^{13}C\{^1H\}$ NMR (125.59 MHz, MeOD): δ 15.0, 15.4, 57.9, 122.4, 122.5, 122.9, 127.4, 128.0, 131.8, 132.1, 132.3, 132.8, 139.5, 140.7, 142.8, 149.4, 157.7. $^{19}F\{^1H\}$ NMR (469.87 MHz, MeOD): δ −78.1, −172.8. $^{11}B\{^1H\}$ NMR (128.20 MHz, MeOD): δ 3.04. HRMS (ESI$^+$) calcd for [2-F]$^+$ ($C_{28}H_{33}BN_3O^+$): 440.2668. found: 440.2679.

Example 2

NMR Study of [2-OH]$^+$ Vs $KHF_2$

Figure 5:
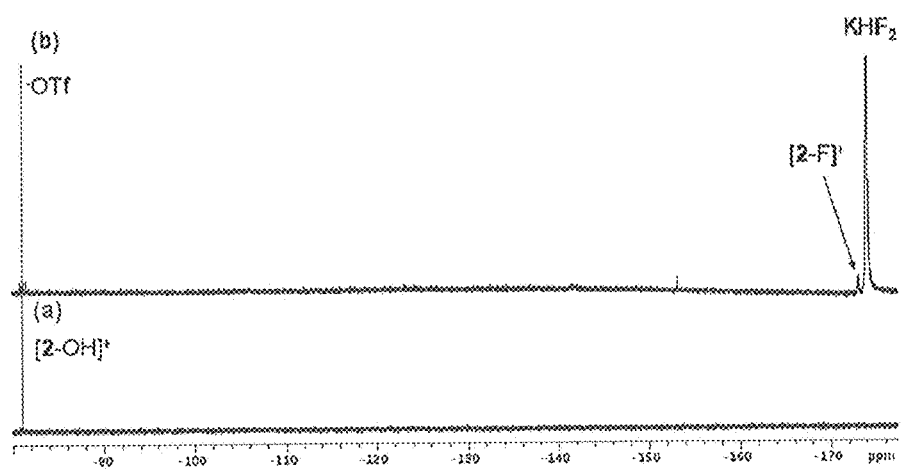
FIG. 5 shows $^{19}$F NMR spectra of compound [2-OH]$^+$ in a 0.95 M DCl solution ($D_2O$/MeOD=1/1) (a) without $KHF_2$ and (b) with excess $KHF_2$.

FIG. 5(a) shows the $^{19}F$ NMR spectrum of [2-OH]$^+$ in acidic $D_2O$/MeOD (v/v=1/1) solution. Upon the addition of $KHF_2$, a signal appeared at −173 ppm within 2 min (FIG. 5(b), indicating the formation of [2-F]$^+$.

Example 3

UV-vis and Fluorescence Measurements of [2-OH]$^+$ and [2-F]$^+$

Figure 6:
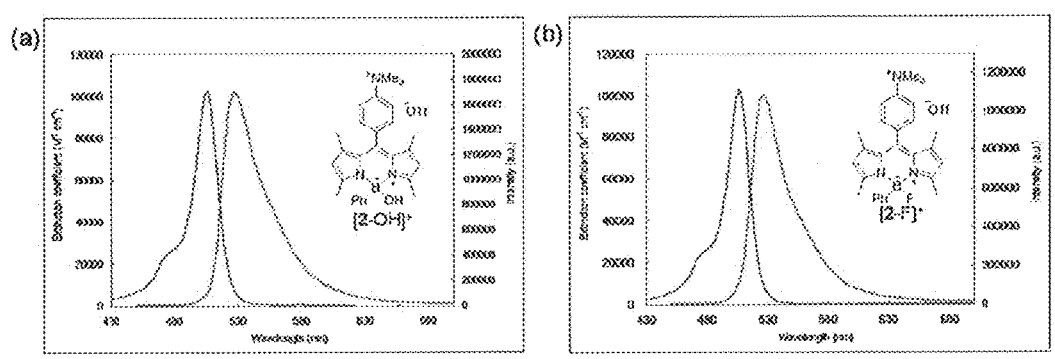
FIG. 6 shows the absorption (blue) and emission (red) spectra of (a) compound [2-OH]$^+$ and (b) compound [2-F]$^+$ in $CH_2Cl_2$.

UV-vis spectra were recorded on an Ocean Optics USB4000 spectrometer with an Ocean Optics ISS light source. Steady state emission spectra were collected at room temperature using a PTI QuantaMaster 4 fluorescence spectrophotometer equipped with a Model 810 PMT detector. The spectra of [2-OH]$^+$ and [2-F]$^+$ were measured in $CH_2Cl_2$ (FIG. 6). Quantum yields were measured using fluorescein as a standard in 0.1 M NaOH solution. Quantum yields obtained for [2-OH]$^+$ and [2-F]$^+$ are 12.1% and 14.3%, respectively.

Example 4

PBS Stability

Figure 7:
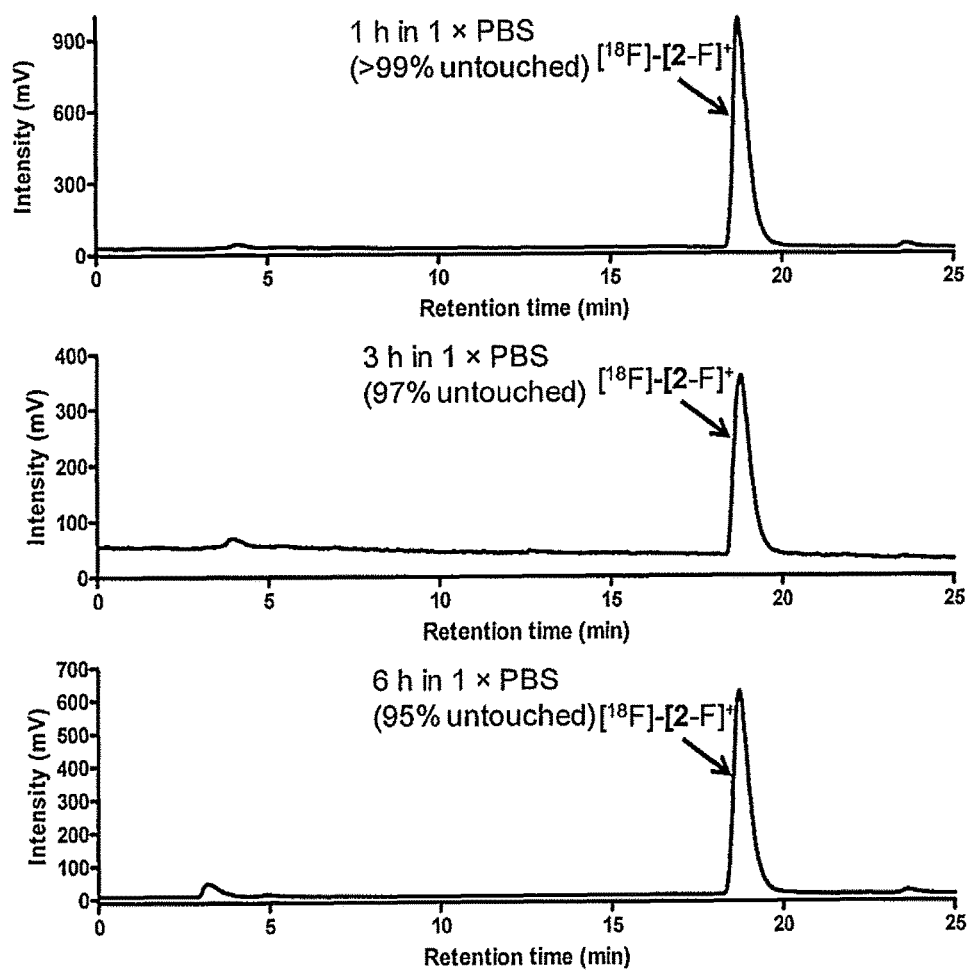
FIG. 7 shows reverse phase HPLC stability studies of compound [$^{18}$F]-[2-F]$^+$ in 1×PBS.
Figure 8:
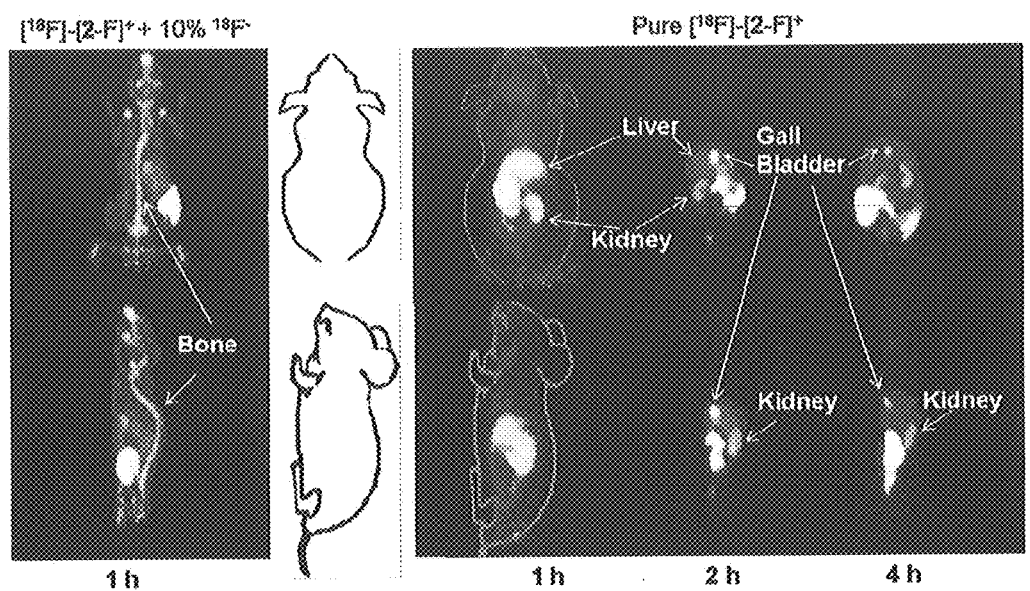
FIG. 8 shows microPET images of a mouse co-injected with [$^{18}$F]-[2-F]$^+$ and ~10% of free $^{18}$F compared to a mouse injected with Pure when compound [$^{18}$F]-[2-F]$^+$.
Figure 9:
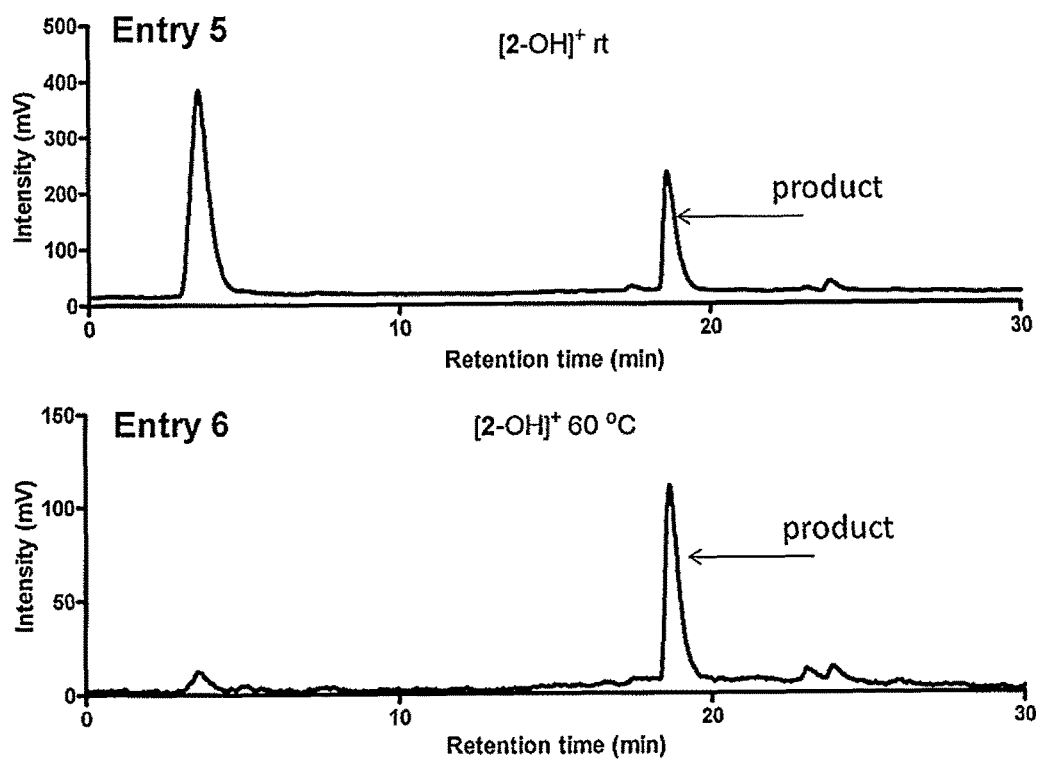
FIG. 9 shows HPLC results for the carrier-free radiofluorination of compound [2-OH]$^+$ in which [2-OH]$^+$ was pretreated with TMSOTf (20 eq.) and then subsequently mixed with a MeCN solution of azeotropically dried [$^{18}$F]-TBAF.
Figure 10:
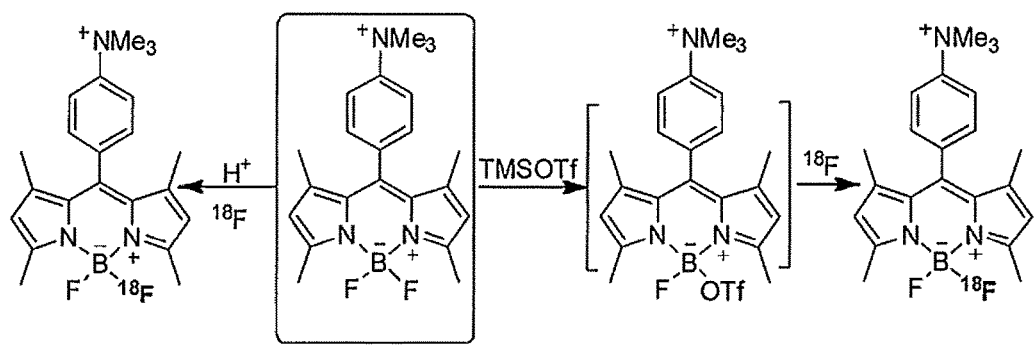
FIG. 10 shows the synthesis of Compound [$^{18}$F]-[3-F] analog under acidic conditions and in organic solve using to Lewis acidic reagent trimethylsilyl triflate.

The [$^{18}$F]-[2-F]$^+$ in nitro stability was tested in 1×PBS. Briefly, [$^{18}$F]-[2-F]$^+$ (about 500 µCi) was incubated in 1×PBS at room temperature. At different time points (1 h, 3 h, and 6 h), an aliquot of [$^{18}$F]-[2-F]$^+$ solution was taken and analyzed by reverse-phase HPLC under identical conditions used for analyzing [$^{19}$F]-[2-F]$^+$ standard. The untouched compound $^{18}$F-2-F was determined to be >99%, 97%, and 95% at 1 h, 3 h, and 6 h, respectively. Representative results are shown in FIG. 7.

Example 5

MicroPET Imaging (as Shown in FIG. 3)

The nude mice were imaged using a microPET $R_4$ rodent model scanner (Concorde Microsystems, Knoxville, Tenn.) in the prone position. The mice were injected with 50-80 µCi of [$^{18}$F]-[2-F]$^+$ via the tail vein. Multiple static scans were obtained at 1, 2, and 4 h post-injection after the mice were anesthetized with 2% isoflurane. The images were reconstructed by a two-dimensional ordered subsets expectation maximum algorithm. After each microPET scan, the images were displayed as 2-D projection to illustrate the whole-body distribution of the tracer. As shown below, significant amounts of bone uptake were observed when [$^{18}$F]-[2-F]$^+$ was co-injected with ~10% of free $^{18}$F. However, no bone uptake even at 4 h post injection if pure [$^{18}$F]-[2-F]$^+$ was injected to the animal. This imaging result demonstrated that [$^{18}$F]-[2-F]$^+$ has reasonable stability in vivo.

Example 6

Fluorescent Imaging (as Shown in FIG. 4)

To cross-evaluate the dual modality tracer $^{18}$F-2-F, ex vivo fluorescence imaging was performed using a Lumina II small-animal imaging system (Xenogen, Alameda, Calif.). After the microPET imaging was done, the nude mouse was sacrificed. Major organs were collected and scanned with the microPET and Limina machines. Fluorescent images were acquired and analyzed using Living Image 2.5 software (Xenogen). The fluorescence images were acquired using a 2-s exposure time (f-stop 4).

Example 7

Carrier-Free Radiofluorination of [2-OH]$^+$

In a typical experiment, [2-OH]$^+$ (500 µg, 0.85 µmol in 100 µl MeCN) was pretreated with TMSOTf (20 eq.) and then subsequently mixed with a MeCN solution (100 µL) of azeotropically dried [$^{18}$F]-TBAF (10 mCi). The reaction was allowed to proceed for 5 min at 60° C. HPLC analysis indicated formation of [$^{18}$F]-[2-F]$^+$ (specific activity≥1.4 Ci/µmol) in a 61%.

TABLE 2

Radiolabeling of [2-OH]$^+$ with [$^{18}$F]-TBAF in MeCN without carrier.

| Entries | Compound | TMSOTf | Temp | Results |
|---|---|---|---|---|
| 1 | [2-OH]$^+$ | None | Rt 15 min | Minimal |
| 2 | [2-OH]$^+$ | None | 75° C. 15 min | Minimal |
| 3 | [2-OH]$^+$ | None | 110° C. 15 min | Minimal |
| 4 | [2-OH]$^+$ | 0.6 equiv | 60° C. 5 min | Yield < 1% |
| 5 | [2-OH]$^+$ | 20 equiv | Rt 5 min | 30% yield* |
| 6 | [2-OH]$^+$ | 20 equiv | 60° C. 5 min | 61% yield* |

*The yield was determined based on the HPLC integration,

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Those skilled in the art will recognize, or be able to ascertain using no more than routine experimentation, many equivalents to the specific embodiments of the method and compositions described herein. Such equivalents are intended to be encompassed by the following claims.

REFERENCES

All publications cited herein, including the foregoing, are expressly incorporated herein by reference for the purpose of describing and disclosing compositions and methodologies that might be used in connection with the invention.

(1) Purser, S.; Moore, P. R.; Swallow, S.; Gouverneur, V. *Chem. Soc. Rev.*, 2008, 37, 320-330; Miller, P. W.; Long, N. J.; Vilar, R.; Gee, A. D. *Angew. Chem. Int. Ed.*, 2008, 47, 8998-9033; Dolle, F.; Roeda, D.; Kuhnast, B.; Lasne, M.-C. *Fluorine and Health*, 2008, 3-65.
(2) Ganguly, B. N.; Mondal, N. N.; Nandy, M.; Roesch, F. *J. Radioanal. Nucl. Chem.*, 2009, 279, 685-698.
(3) Mu, L.; Hahne, A.; Schubiger, P. A.; Ametamey, S. M.; Graham, K.; Cyr, J. E.; Dinkelborg, L.; Stellfeld, T.; Srinivasan, A.; Voigtmann, U.; Klar, U. *Angew. Chem. Int. Ed.*, 2008, 47, 4922-4925; Höhne, A.; Mu, L.; Honer, M.; Schubiger, P. A.; Ametamey, S. M.; Graham, K.; Stellfeld, T.; Borkowski, S.; Berndorff, D.; Klar, U.; Voigtmann, U.; Cyr, J. E.; Friebe, M.; Dinkelborg, L.; Srinivasan, A. *Bioconjugate Chem.*, 2008, 19, 1871-1879; Schirrmacher, E.; Wangler, B.; Cypryk, M.; Bradtmöller, G.; Schäfer, M.; Eisenhut, M.; Jurkschat, K.; Schirrmacher, R. *Bioconjugate Chem.*, 2007, 18, 2085-2089; Schirrmacher, R.; Bradmoeller, G.; Schirrmacher, E.; Thews, O.; Tillmanns, J.; Siessmeier, T.; Bucholz, H. G.; Bartenstein, P.; Waengler, B.; Niemeyer, C. M.; Jurkschat, K. *Angew. Chem., hit. Ed.*, 2006, 45, 6047-6050; McBride, W. J.; Sharkey, R. M.; Karacay, H.; D'Souza, C. A.; Rossi, E. A.; Laverman, P.; Chang, C.-H.; Boerman, O. C.; Goldenberg, D. M. *J. Nucl. Med.*, 2009, 50, 991-998; McBride, W. J.; D'Souza, C. A.; Sharkey, R. M.; Karacay, H.; Rossi, E. A.; Chang, C.-H.; Goldenberg, D. M. *Bioconjugate Chem.*, 2010, 21, 1331-1340.
(4) Tsien, R. Y. *Nat. Cell Biol.*, 2003, SS16-SS21.
(5) Ducongé, F.; Pons, T.; Pestourie, C.; Hérin, L.; Thézé, B.; Gombert, K.; Mahler, B.; Hinnen, F.; Kühnast, B.; Dollé, F.; Dubertret, B.; Tavitian, B. *Bioconjugate Chem.*, 2008, 19, 1921-1926.
(6) Ting, R.; Aguilera, T. A.; Crisp, J. L.; Hall, D. J.; Eckelman, W. C.; Vera, D. R.; Tsien, R. Y. *Bioconjugate Chem.*, 2010, 21, 1811-1819.
(7) Loudet, A.; Burgess, K. *Chem. Rev.*, 2007, 107, 4891-4932; Ulrich, G.; Ziessel, R.; Harriman, A. *Angew. Chem., Int. Ed.*, 2008, 47, 1184-1201.
(8) Hudnall, T. W.; Gabbaï, F. P. *Chem. Commun.*, 2008, 4596-4597.
(9) Bonnier, C.; Piers, W. E.; Parvez, M.; Sorensen, T. S. *Chem. Commun.*, 2008, 4593-4595; Bonnier, C.; Piers, W. E.; Al-Sheikh Ali, A.; Thompson, A.; Parvez, M. *Organometallics*, 2009, 28, 4845-4851.
(10) Hudnall, T. W.; Lin, T.-P.; Gabbaï, F. P. *J. Fluorine Chem.*, 2010, 131, 1182-1186.
(11) Qi, X.; Kim, S. K.; Jun, E. J.; Xu, L.; Kim, S.-J.; Yoon, J. *Bull. Korean Chem. Soc.*, 2007, 28, 2231-2234.
(12) Tasior, M.; Murtagh, J.; Frimannsson, D. O.; McDonnell, S. O.; O'Shea, D. F. *Org. Biomol. Chem.*, 2010, 8, 522-525; Hudnall, T. W.; Gabbaï, F. P. *J. Am. Chem. Soc.*, 2007, 129, 11978-11986; Chiu, C.-W.; Kim, Y.; Gabbaï, F. P. *J. Am. Chem. Soc.*, 2009, 131, 60-61.
(13) Wade, C. R.; Broomsgrove, A. E. J.; Aldridge, S.; Gabbaï, F. P. *Chem. Rev.*, 2010, 110, 3958-3984.
(14) Ting, R.; Harwig, C.; auf dem Keller, U.; McCormick, S.; Austin, P.; Overall, C. M.; Adam, M. J.; Ruth, T. J.; Perrin, D. M. *J. Am. Chem. Soc.*, 2008, 130, 12045-12055; auf dem Keller, U.; Bellac, C. L.; Li, Y.; Lou, Y.; Lange, P. F.; Ting, R.; Harwig, C.; Kappelhoff, R.; Dedhar, S.; Adam, M. J.; Ruth, T. J.; Bénard, F.; Perrin, D. M.; Overall, C. M. *Cancer Res.*, 2010, 70, 7562-7569.
(15) Van de Bittner, G. C.; Dubikovskaya, E. A.; Bertozzi, C. R.; Chang, C. J. *Proc. Natl. Acad. Sci. U.S.A., Early Ed.*, 2010, 1-6.
(16) Cai, L.; Lu, S.; Pike, V. W. *Eur. J. Org. Chem.*, 2008, 2853-2873.

We claim:

1. A composition having an imaging probe therein comprising:
   the lewis acid $SnCl_4$; and
   at least one compound selected from the group consisting of compounds of Formula I, including salts, hydrates and solvates thereof:

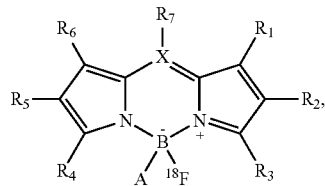

Formula I the compounds of Formula X, including salts, hydrates and solvates thereof

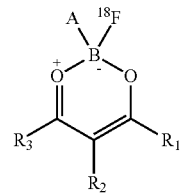

Formula X the compounds of Formula XII, including salts, hydrates and solvates thereof

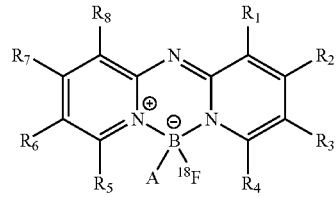

Formula XII wherein $R_1$, $R_2$, $R_3$, $R_4$, $R_5$, $R_6$, and $R_7$ may be independently selected from one or more of the group consisting of hydrogen, halogen, hydroxy, alkoxy, nitro, substituted and unsubstituted amino, cycloalkyl, carboxy, carboxylic acids and esters thereof, cyano, haloalkyl, aryl, including phenyl and aminophenyl, azide, alkyne and heteroaryl;

X is selected from the group consisting of C and N;

A is selected from one or more of the group consisting of hydrogen, halogen, hydroxy, alkoxy, nitro, and substituted and unsubstituted amino, alkyl, cycloalkyl, carboxy, carboxylic acids and esters thereof, cyano, haloalkyl, aryl, including phenyl and aminophenyl, and heteroaryl.

2. The composition according to claim 1, wherein the composition comprises at least one compound of Formula I, including salts, hydrates and solvates thereof:

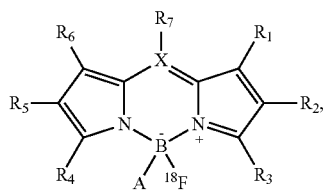

Formula I wherein $R_1$, $R_2$, $R_3$, $R_4$, $R_5$, $R_6$, and $R_7$ may be independently selected from one or more of the group consisting of hydrogen, halogen, hydroxy, alkoxy, nitro, substituted and unsubstituted amino, cycloalkyl, carboxy, carboxylic acids and esters thereof, cyano, haloalkyl, aryl, including phenyl and aminophenyl, azide, alkyne and heteroaryl;

X is selected from the group consisting of C and N;

A is selected from one or more of the group consisting of hydrogen, halogen, hydroxy, alkoxy, nitro, and substituted and unsubstituted amino, alkyl, cycloalkyl, carboxy, carboxylic acids and esters thereof, cyano, haloalkyl, aryl, including phenyl and aminophenyl, and heteroaryl.

3. The composition according to claim 2, wherein the composition comprises at least one compound selected from the group consisting of Formulas IV and VI, including salts, hydrates and solvates thereof:

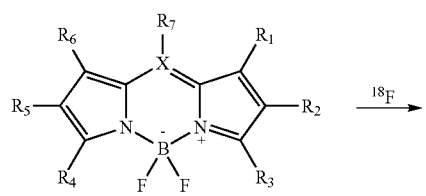

Formula III

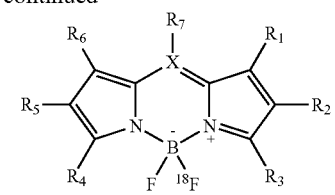

Formula IV

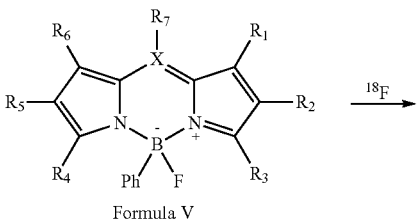

Formula V

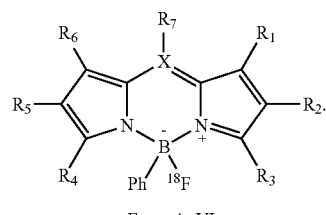

Formula VI

4. The composition according to claim 3, further comprising at least one compound selected from the group consisting of:

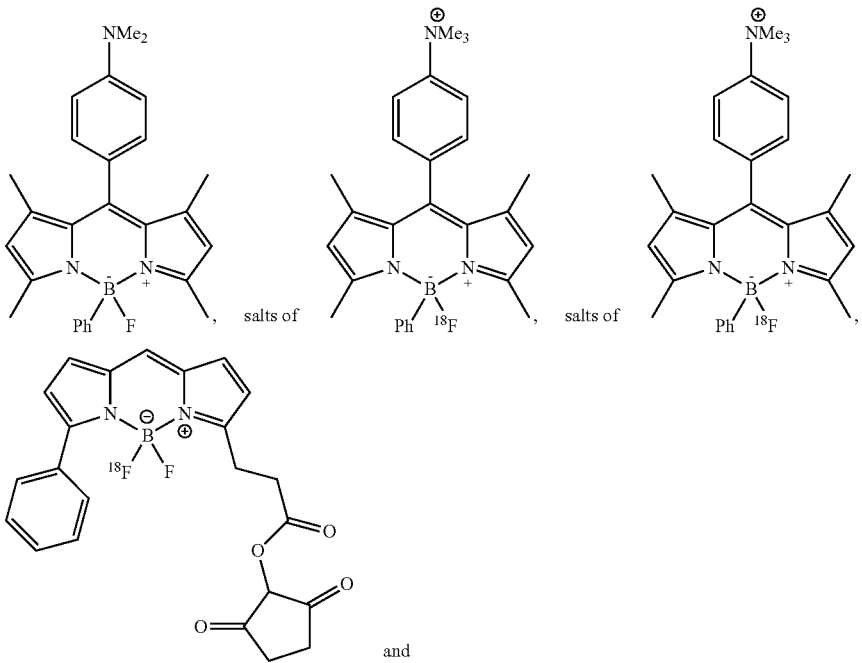

and

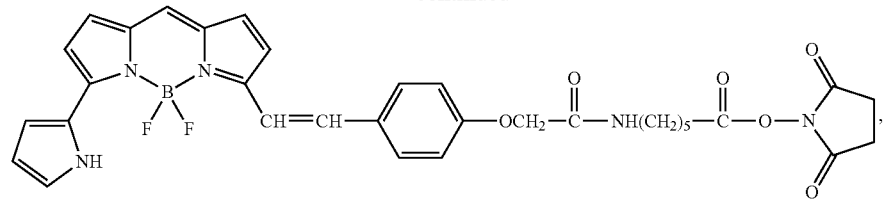

wherein at least one of the fluorines in a B—F bond in the compound is $^{18}$F.

5. The composition according to claim 1, wherein the compound is conjugated to a targeting moiety.

6. The composition according to claim 5, wherein the compound is a compound according to Formula 1, including salts, hydrates and solvates thereof:

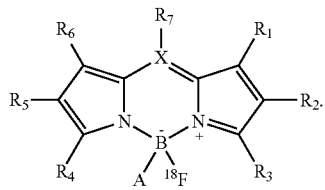

Formula I

7. The composition according to claim 6, wherein the targeting moiety is a peptide.

8. The composition according to claim 7, wherein the targeting moiety is an RGD peptide.

9. The composition according to claim 8, wherein the targeting moiety is a cyclic RGD peptide.

10. The composition according to claim 7, wherein the peptide is selected from the group consisting of:

RGD

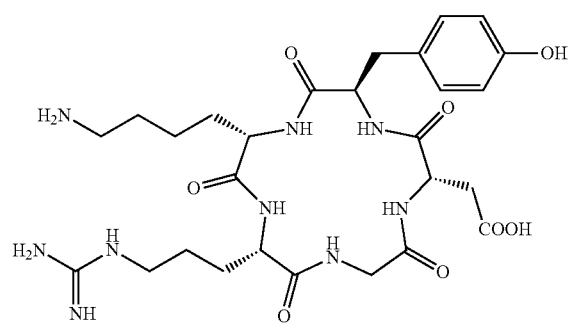

and

PRGD$_2$

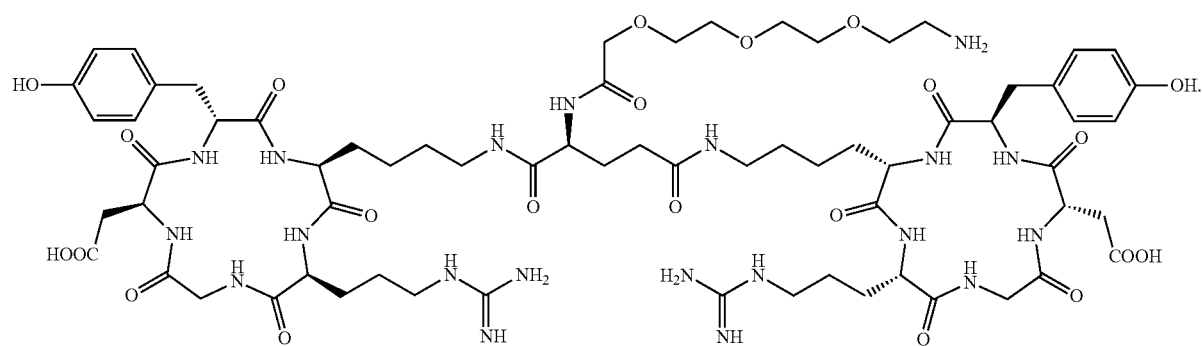

* * * * *